United States Patent [19]

Tamai et al.

[11] Patent Number: 4,477,437

[45] Date of Patent: Oct. 16, 1984

[54] SUBSTANCES HAVING CARCINOSTATIC AND IMMUNOSTIMULATING ACTIVITY

[75] Inventors: Kenzo Tamai, Kanazawa; Isamu Saikawa, Toyama; Takashi Yasuda, Toyama; Shohachi Murakami, Toyama; Toyoo Maeda, Kanazawa; Hisatsugu Tsuda, Toyama; Hiroshi Sakai, Takaoka; Masatoshi Sugita, Toyama; Yoshiko Yamamoto, Namekawa; Hisashi Minami; Takako Hori, both of Toyama, all of Japan

[73] Assignee: Toyama Chemical Co., Ltd., Tokyo, Japan

[21] Appl. No.: 347,871

[22] Filed: Feb. 11, 1982

[30] Foreign Application Priority Data

| Feb. 19, 1981 | [JP] | Japan | 56-22270 |
| Feb. 19, 1981 | [JP] | Japan | 56-22271 |
| Feb. 19, 1981 | [JP] | Japan | 56-22272 |
| Feb. 19, 1981 | [JP] | Japan | 56-22273 |
| Feb. 19, 1981 | [JP] | Japan | 56-22274 |
| Feb. 19, 1981 | [JP] | Japan | 56-22275 |
| Feb. 19, 1981 | [JP] | Japan | 56-22276 |
| Feb. 19, 1981 | [JP] | Japan | 56-22277 |

[51] Int. Cl.$^3$ .................... A61K 31/715; C08B 37/00
[52] U.S. Cl. .................... 424/116; 424/177; 424/180; 536/1.1; 536/123
[58] Field of Search .......... 424/180, 177, 116; 536/1.1, 123

[56] References Cited

U.S. PATENT DOCUMENTS

4,237,266  12/1980  Sugiura et aql. ............ 536/1.1
4,357,323  11/1982  Soma et al. ................. 536/1.1

OTHER PUBLICATIONS

Rietschel, "Chem. Abst.", vol. 85, 1976, p. 88,869(d).
Falkler et al., "Chem. Abst.", vol. 92, 1980, p. 122,508(s).
Mongiello et al., "Chem. Abst.", vol. 92, 1980, p. 122,509(t).

*Primary Examiner*—Johnnie R. Brown
*Attorney, Agent, or Firm*—Oblon, Fisher, Spivak, McClelland & Maier

[57] ABSTRACT

Novel TF-2 substances having carcinostatic and immunostimulating activity, which are obtained from a culture or its supernatant fluid prepared by culturing bacteria belonging to Fusobacterium genus. Said substances are useful for the treatment of cancerous diseases of the mammals including human being. This disclosure concerns such substances and a process for preparing the same and a carcinostatic agent containing the same.

12 Claims, 31 Drawing Figures

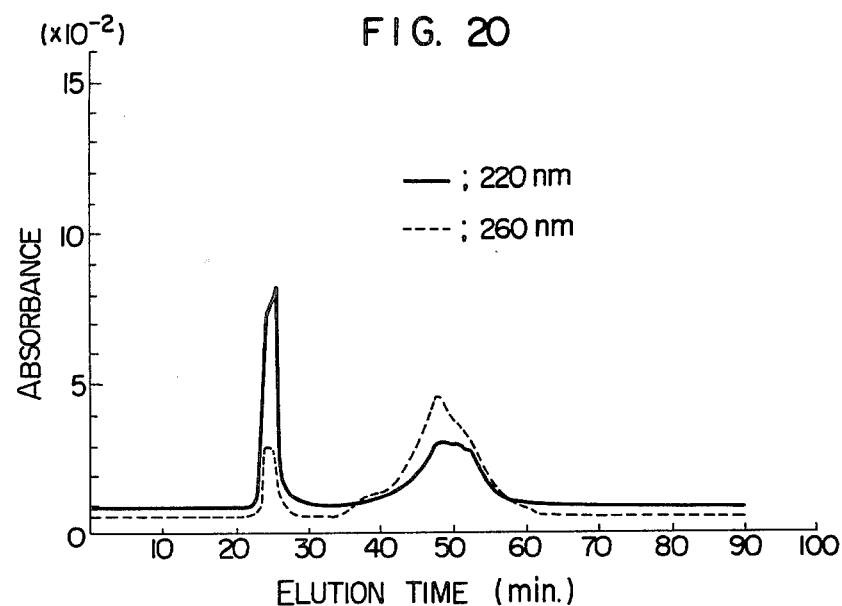
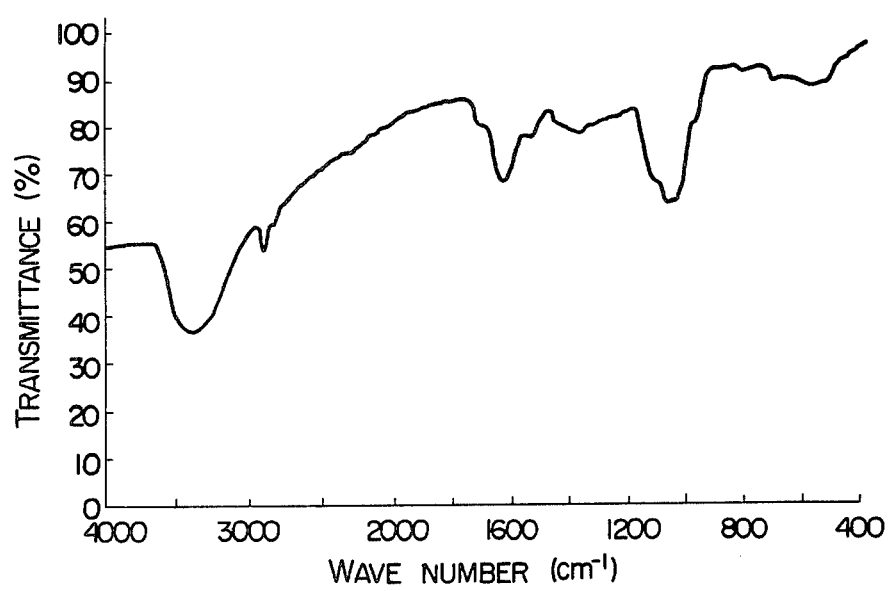

SUBSTANCES HAVING CARCINOSTATIC AND IMMUNOSTIMULATING ACTIVITY

This invention relates to a process for producing novel substances having carcinostatic and immunostimulating activity which comprises culturing under anaerobic conditions TF-2-substance-producing bacteria belonging to Fusobacterium genus and obtaining the TF-2 substances from the culture or its supernatant fluid (said novel substance being hereinafter referred to as TF-2 substance), relates to the TF-2 substances obtained [hereinafter include TF-210, 220, 230, 240, 250, 300 (310, 320, 330), 340 and 350], and relates to a carcinostatic agent containing the same.

In recent years, there has come to be extensively used, as a remedy for patients with various types of cancer, a remedy comprising enhancing immunological function of the host and obtaining a carcinostatic effect with the assistance of the immunological function. As antitumor agents used for such a remedy, there are known components obtained from organisms of various bacteria or culture of various bacteria or polysaccharides obtained from fruit bodies of Basidiomycetes or cultured fungus bodies thereof.

The present inventors have examined the pharmacological activity of a supernatant fluid obtained by culturing bacteria belonging to Fusobacterium genus and removing the organisms from the culture to find that a specific component obtained from the supernatant fluid has a carcinostatic activity; that said component has an indirect carcinostatic activity by increasing the host mediated antitumor activity or the immunity of the host and utilizing the assistance of the immunity; and that said component is very low in toxicity and can be obtained also by treating the culture.

An object of this invention is to provide a process comprising culturing bacteria belonging to Fusobacterium genus under anaerobic conditions and collecting novel TF-2 substances having carcinostatic and immunostimulating activities from the resulting culture or the supernatant fluid thereof.

Another object of this invention is to provide said TF-2 substances.

A further object of this invention is to provide a carcinostatic agent containing said TF-2 substances.

Other objects and advantages of this invention will become apparent from the following description.

As the bacteria utilized in this invention, any TF-2 substance-producing bacteria belonging to Fusobacterium genus may be used, and, for example, Fusobacterium nucleatum are preferably used. Concretely, Fusobacterium nucleatum TF-031 (FERM 5077; ATCC 31647) and strains which are considered to have said properties in a general knowledge of microbiology, namely, spontaneous mutants or artificially modified strains are used.

The bacteriological properties of Fusobacterium nucleatum TF-031 are as follows:

(I) Form
 (1) Form of the cells: spindle-shaped (FIG. 1)
 (2) Polymorphism of the cells: absent
 (3) Motility: absent
 (4) Spores: absent
 (5) Gram stain: Gram-negative
 (6) Acid resistance: negative
(II) Growing conditions in a culture medium
 (1) TF-a agar plate and slant culture medium
  External form: a round shape
  Size: about 1 mm
  Protuberance: hemispherical shape
  Structure: dewdrop-like
  Surface: smooth
  Edges: smooth
  Color: milky yellowish white
  Transparency: opaque
 (2) TF-a liquid culture medium
  Degree of growth: vigorous
  Turbidity: coagulum
  Precipitate: none
  Growth of surface: none, no growth to a depth of about 5 mm
  Gas: none
(III) Physiological properties
 (1) Production of hydrogen sulfide: +
 (2) Reduction of nitrates: −
 (3) Production of butyric acid: +
 (4) Production of indole: +
 (5) Urease: −
 (6) Catalase: −
 (7) Hydrolysis of starch: −
 (8) Behavior to oxygen: anaerobic
 (9) Production of ammonia: +
 (10) Production of carbon dioxide: +
 (11) Range for growth: pH 5.0–8.5, temperature 30°–45° C.
 (12) Production of gas from saccharides:
  L-arabinose (−), D-xylose (−), D-glucose (−), D-mannose (−), D-fructose (−), D-galactose (−), malt sugar (−), sucrose (−), trehalose (−), sorbitol (−), mannitol (−), inositol (−), glycerol (−), starch (−)

The novel TF-2 substances of this invention are produced, for example, in the following manner.

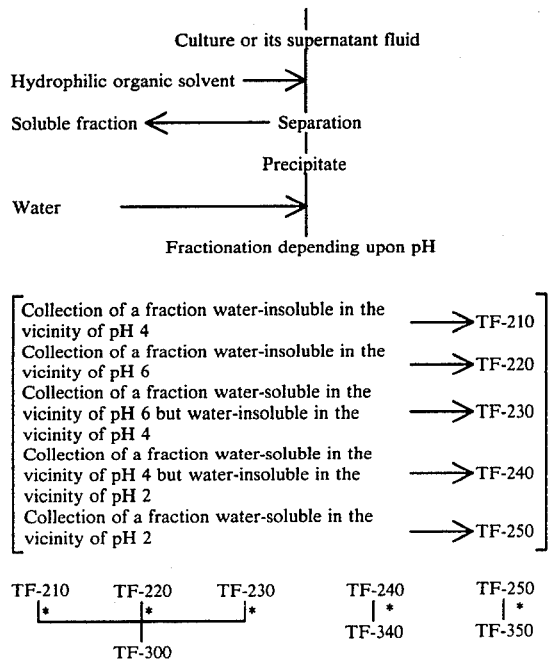

-continued

| Culture of TF-2 substance-producing bacteria belonging to *Fusobacterium nucleatum* | | |
|---|---|---|
| TF-310 | TF-320 | TF-330 |

*Deproteinization

The above-mentioned production process is illustrated below as follows:

(1) Culture of bacteria

The culture of bacteria belonging to Fusobacterium genus is carried out by a conventional method for culturing anaerobic bacteria. That is to say, a culture medium containing a nitrogen source such as bovine brain-heart extracts, various peptones, or the like; a vitamine source such as yeast extract or the like; an inorganic salt such as sodium chloride or the like; a carbon source such as glucose, lactose or the like; a reducing agent such as L-cystine, sodium sulfite, thioglycolate or the like, is adjusted to a pH of 6 to 8.5, preferably 6.5 to 7.5, and the bacteria are inoculated on the culture medium, after which steady-state culture is carried out under anaerobic conditions at 30° to 42° C., preferably 32° to 37° C., for 1 to 5 days, preferably 24 to 96 hours. In particular, it is desirable to use the culture medium described in Table 1 (hereinafter referred to as TF culture medium). However, the brain-heart-infusion which is a bovine brain-heart extract is not always necessary as a carbon source and may be replaced by a heart infusion which is a bovine heart extract, a beef extract, a fish extract, a corn steep liquor, or the like. Among the various peptones, proteose peptone and phytone peptone are not always necessary, and the trypticase peptone may be replaced by polypeptone.

When agar is not used, it is desirable to carry out stirring culture.

TABLE 1

| Constituents of culture medium (g/l) | TF-a | TF-b | TF-c | TF-d | TF-e | TF-f |
|---|---|---|---|---|---|---|
| Trypticase peptone | 17 | 17 | 17 | 17 | 17 | 17 |
| Phytone peptone | 3 | 3 | 1.5 | — | — | — |
| Proteose peptone | 10 | 5 | 5 | — | — | — |
| Brain-heart-infusion | 35 | 17.5 | — | — | — | — |
| Heart infusion | — | — | 25 | 20 | 10 | 15 |
| Yeast extract | 3 | 3 | 3 | 3 | 3 | 3 |
| Sodium chloride | 7.5 | 7.5 | 7.5 | 7.5 | 7.5 | 7.5 |
| Glucose | 6 | 6 | 6 | 12 | 12 | 12 |
| Lactose | 5 | 5 | 5 | 10 | 10 | 10 |
| L-Cystine | 0.25 | 0.5 | 0.5 | — | — | — |
| Sodium sulfite | 0.1 | 0.1 | 0.1 | 0.1 | 0.1 | 0.1 |
| Thioglycolate | 0.5 | 0.5 | 0.5 | 0.5 | 0.5 | 0.5 |
| Agar | 0 or 0.7 | 0 or 0.7 | 0 or 0.7 | 0 or 0.7 | 0 or 0.7 | 0 or 0.7 |

(2) Collection of a supernatant fluid from the culture (removal of the organisms)

The organisms are removed from the culture obtained above to get a supernatant fluid. For the removal of the organisms, a conventional method, for example, centrifugation and a filtration method using a filter aid, such as Hyflo-Super-Cel, may be used, and in particular, a centrifugation method is preferable from the viewpoint of operations, the degree of removal of the organisms, and the yield of the supernatant fluid.

(3) Collection of carcinostatic substance TF-2

(i)(a) A hydrophilic organic solvent is added to the supernatant fluid obtained above or the culture, and the precipitate formed is collected. At this time, the supernatant fluid or the culture is preferably adjusted to pH 1.5 to 7, preferably the vicinity of pH 2 (pH 1.5 to 2.5). The hydrophilic organic solvent includes, for example, alcohols such as ethanol, methanol and the like, and ketones such as acetone and the like, though alcohols, particularly ethanol, brings about the best result. The hydrophilic organic solvent is suitably added so that its concentration may be 30 to 80%, particularly 50 to 80%, by volume. After the addition of the hydrophilic organic solvent, the resulting mixture is allowed to stand at a low temperature, preferably at about 5° C., for several hours to several days to complete the formation of the precipitate.

The thus formed precipitate is separated by conventional procedures such as decantation, centrifugation, filtration and the like.

(b) To the precipitate separated above is added water generally in a quantity 5 to 20 times that of the precipitate, and fractionate the precipitate depending upon pH. Specifically, this procedure is carried out as follows:

(b-1) The above mixture of the precipitate and water is adjusted to a pH of 7.5 to 8. After removal, if necessary, of the insoluble portion, the mixture is adjusted to the vicinity of pH 4 (3.5 to 4.5). The resulting water-insoluble and water-soluble portions are separated from each other by the use of a conventional method such as centrifugation, filtration, or the like. The water-insoluble portion thus obtained (TF-210) has the properties shown in Table 2.

(b-2) Separately, to the precipitate obtained in above (a) is added water generally in a quantity 5 to 20 times that of the precipitate. The mixture is adjusted to pH 7.5 to 8. After removal, if necessary, of the insoluble portion, the mixture is adjusted to the vicinity of pH 6 (5.5 to 6.5). The resulting water-insoluble and water-soluble portions are separated from each other by a conventional method such as centrifugation, filtration, or the like. The water-insoluble portion thus obtained (TF-220) has the properties shown in Table 2.

(b-3) The water-soluble portion separated in above (b-2) is adjusted to the vicinity of pH 4 (3.5 to 4.5). The precipitate and the water-soluble portion obtained are separated from each other by a conventional method such as centrifugation, filtration, or the like. The precipitate thus obtained (TF-230) has the properties shown in Table 2.

(b-4) The water-soluble portion separated in above (b-1) or (b-3) is adjusted to the vicinity of pH 2 (1.5 to 2.5), upon which a precipitate is formed. This precipitate is separated from its water-soluble portion by a conventional method such as centrifugation, filtration or the like. The precipitate thus obtained (TF-240) has the properties shown in Table 2.

(b-5) To the precipitate obtained in above (a) is added water generally in a quantity 5 to 20 times that of the precipitate and the pH of the mixture is adjusted to, for example, 7.5 to 8. Then, the pH is further adjusted to the vicinity of pH 2 (1.5 to 2.5). To the water-soluble portion thus obtained or to the water-soluble portion separated in above (b-4) is added, if necessary after concentrating the quantity of the water-soluble portion to one third to one seventh thereof, a hydrophilic organic solvent, preferably an alcohol so that its concentration becomes 20 to 80%, preferably 20 to 60%, by volume.

Collection of the resulting precipitate gives TF-250. The carcinostatic substance TF-250 thus obtained has the properties shown in Table 2.

The carcinostatic substances TF-210, TF-220, TF-230, TF-240 and TF-250 thus obtained may each be subjected several times to the same fractionation depending upon pH for purification. The carcinostatic substances thus obtained may each be converted by a conventional method to pharmaceutically acceptable salts such as alkali metal salts, for example, sodium salts, potassium salts and the like and alkaline earth metal salts, for example, magnesium salts, calcium salts and the like.

(ii) The fractions having carcinostatic activity obtained as mentioned in above (i), TF-210, TF-220, TF-230, TF-240 and TF-250 are each subjected to deproteinization treatment according to a conventional method to obtain TF-300 (TF-310, TF-320 and TF-330), TF-340 and TF-350. For the deproteinization treatment, there may be used methods known in the art, and particularly preferred is such a method as decomposition with proteolytic enzymes. When it is desired that the deproteinization is carried out by a treatment with a proteolytic enzyme, it is sufficient that each of the fractions having carcinostatic activity obtained in above (i) is dissolved or suspended in water or a buffer solution, a protein-decomposing enzyme is added to the resulting solution or suspension, and the enzyme-treatment is conducted in a conventional manner.

As the proteolytic enzymes, there may be mentioned pronase, papain, trypsin, chemotrypsin, and the like. Pronase and trypsin are preferred. It is preferable that, prior to or during the enzyme treatment, the aqueous solution be adjusted to and maintained at a pH of 7 to 8. For this purpose, there may be used sodium hydroxide, potassium hydroxide, sodium carbonate, sodium hydrogen carbonate and the like. In order to prevent the putrefaction of the reaction mixture during the enzyme treatment, it is desirable to add a small quantity of an organic solvent such as chloroform, toluene or the like. The enzyme is usually used in an amount of about 1 to 2% by weight based on the weight of the powder (solid) to be subjected to the enzyme treatment.

The above enzyme treatment is usually carried out at 30° to 40° C. for 1 to 72 hours, preferably 24 to 48 hours. It may also be conducted by first adding, for example, about 1% by weight of an enzyme to a powder (solid) and subjecting the powder (solid) to enzyme treatment for 1 to 24 hours and subsequently adding about 1% by weight of the enzyme again for further enzyme treatment.

After the above enzyme treatment, insolubles are, if necessary, removed by a procedure such as centrifugation, filtration, or the like, after which from the water-soluble portion thus obtained are collected respective fractions of carcinostatic substances TF-300 (TF-310, TF-320, TF-330), TF-340 and TF-350. In such a manner, TF-310 can be obtained from TF-210, TF-320 from TF-220, TF-330 from TF-230, TF-340 from TF-240 and TF-350 from TF-250. The isolation of the fractions of these TF-300 (TF-310, TF-320, TF-330), TF-340 and TF-350 may be conducted by at least one of fractionation depending upon pH, separate precipitation from a hydrophilic organic solvent, fractionation with an ion exchanger, ultrafiltration and the like. Alternatively, one or more of these operations may be repeated several times. Specifically, the present carcinostatic substances TF-300 (TF-310, TF-320, TF-330), TF-340 and TF-350 are obtained by adjusting the pH of the above water-soluble portion to preferably, a pH of not more than 2.5 (if necessary, trichloroacetic acid may be added), removing the resulting precipitate, adding to the soluble portion a hydrophilic organic solvent such as an alcohol so that its concentration becomes 30 to 80%, preferably 60 to 80%, by volume, collecting the resulting precipitate which is the fraction of the objective substance, subsequently treating, if necessary, this precipitate with a strong anion exchange resin such as Dowex 1 type (trade name), Amberlite IRA-400 (trade name), or the like (this treatment may be conducted several times) to collect the unadsorbed fractions, subjecting, if necessary, the fractions to ultrafiltration [for example, Toyo Ultrafilter UK-50 (nominal molecular weight cutoff: 50,000) or Toyo Ultrafilter UK-200 (nominal molecular weight cutoff: 200,000)], and then subjecting them to such a treatment as concentration, desalting, drying or precipitation from a hydrophilic organic solvent, or the like. The thus obtained carcinostatic substances TF-300 (TF-310, TF-320, TF-330), TF-340 and TF-350 have the properties shown in Table 2.

The carcinostatic substances TF-300 (TF-310, TF-320, TF-330), TF-340 and TF-350 may be converted to pharmaceutically acceptable salts according to a conventional method. Specifically, there may be mentioned, for example, alkali metal salts such as sodium salts, potassium salts and the like and alkaline earth metal salts such as magnesium salts, calcium salts, and the like, as said pharmaceutically acceptable salts.

TABLE 2

| Fraction | Appearance | Pharmacological action | Solubility |
| --- | --- | --- | --- |
| TF-210 | Grayish white-light brown powder | This fraction inhibited the proliferation of Ehrlich ascites tumor, Ehrlich solid tumor, Sarcoma 180 and B-16 Melanoma of mouse and had an immunostimulating activity. | Insoluble in methanol, ethanol, acetone, benzene, chloroform, ethyl acetate and diethyl ether. |
| TF-220 | Grayish white-light brown powder | This fraction inhibited the proliferation of Ehrlich ascites tumor, Ehrlich solid tumor, Sarcoma 180 and B-16 Melanoma of mouse and had an immunostimulating activity. | Insoluble in methanol, ethanol, acetone, benzene, chloroform, ethyl acetate and diethyl ether. |
| TF-230 | Grayish white-light brown powder | This fraction inhibited the proliferation of Ehrlich ascites tumor, Ehrlich solid tumor, Sarcoma 180 and B-16 Melanoma of mouse and had an immunostimulating activity. | Insoluble in methanol, ethanol, acetone, benzene, chloroform, ethyl acetate and diethyl ether. |
| TF-240 | Grayish white-light brown powder | This fraction inhibited the proliferation of Ehrlich ascites tumor, Ehrlich solid tumor, Sarcoma 180 | Insoluble in methanol, ethanol, acetone, benzene, chloroform, |

TABLE 2-continued

| Fraction | | | |
|---|---|---|---|
| TF-250 | Grayish white-light brown powder | and B-16 Melanoma of mouse and had an immunostimulating activity. This fraction inhibited the proliferation of Ehrlich ascites tumor, Ehrlich solid tumor, Sarcoma 180 and B-16 Melanoma of mouse and had an immunostimulating activity. | ethyl acetate and diethyl ether. Soluble in water, and insoluble in methanol, ethanol, acetone, benzene, chloroform, ethyl acetate and diethyl ether. |
| TF-300 | Grayish white-light brown powder | This fraction inhibited the proliferation of Ehrlich ascites tumor, Ehrlich solid tumor, Sarcoma 180 and B-16 Melanoma of mouse and had an immunostimulating activity. | Soluble in water, and insoluble in methanol, ethanol, acetone, benzene, chloroform, ethyl acetate and diethyl ether. |
| TF-310 | Grayish white-light brown powder | This fraction inhibited the proliferation of Ehrlich ascites tumor, Ehrlich solid tumor, Sarcoma 180 and B-16 Melanoma of mouse and had an immunostimulating activity. | Soluble in water, and insoluble in methanol, ethanol, acetone, benzene, chloroform, ethyl acetate and diethyl ether. |
| TF-320 | Grayish white-light brown powder | This fraction inhibited the proliferation of Ehrlich ascites tumor and Sarcoma 180 of mouse and had an immunostimulating activity. | Soluble in water, and insoluble in methanol, ethanol, acetone, benzene, chloroform, ethyl acetate and diethyl ether. |
| TF-330 | Grayish white-light brown powder | This fraction inhibited the proliferation of Ehrlich ascites tumor of mouse and had an immunostimulating activity. | Soluble in water, and insoluble in methanol, ethanol, acetone, benzene, chloroform, ethyl acetate and diethyl ether. |
| TF-340 | Grayish white-light brown powder | This fraction inhibited the proliferation of Ehrlich ascites tumor of mouse and had an immunostimulating activity. | Soluble in water, and insoluble in methanol, ethanol, acetone, benzene, chloroform, ethyl acetate and diethyl ether. |
| TF-350 | Grayish white-light brown powder | This fraction inhibited the proliferation of Ehrlich ascites tumor of mouse and had an immunostimulating activity. | Soluble in water, and insoluble in methanol, ethanol, acetone, benzene, chloroform, ethyl acetate and diethyl ether. |

| | | Properties | | | |
|---|---|---|---|---|---|
| | | Infrared absorption spectra (KBr method) | Elementary analysis values | | |
| Fraction | Decomposing point | $(cm^{-1})$ | C (%) | H (%) | N (%) |
| TF-210 | This fraction did not show sharp melting point and decomposed at 160° to 235° C. | The spectrum has an absorption bands in the vicinity of 3600–3200, 2950–2920, 1680–1620, 1550–1510, 1440, 1380 1240–1220 and 1120–1020 $cm^{-1}$. | 40–43 | 5–7 | 9–10 |
| TF-220 | This fraction did not show sharp melting point and decomposed a 160° to 240° C. | The spectrum has absorption bands in the vicinity of 3600–3200, 2950–2920, 1680–1620, 1550–1510, 1440, 1380, 1240–1220 and 1120–1020 $cm^{-1}$. | 40–42 | 5–7 | 7–9 |
| TF-230 | This fraction did not show sharp melting point and decomposed at 185° to 225° C. | The spectrum has absorption bands in the vicinity of 3600–3200, 2950–2920, 1680–1620, 1550–1510, 1440, 1380, 1240–1220 and 1120–1020 $cm^{-1}$. | 42–45 | 5–7 | 10–11 |
| TF-240 | This fraction did not show sharp melting point and decomposed at 200° to 215° C. | This spectrum has absorption bands in the vicinity of 3600–3200, 2950–2920, 1680–1620, 1550–1520, 1410–1360, 1280–1210, 1060, 960 and 820 $cm^{-1}$. | 35–38 | 4–5 | 12–14 |
| TF-250 | This fraction did not show sharp melting point and decomposed at 165° to 210° C. | This spectrum has absorption bands in the vicinity of 3600–3200, 2950–2920, 1680–1620, 1550–1510, 1410–1380, 1240–1210, 1150–1120, 1080–1020, 980 and 810 $cm^{-1}$. | 30–33 | 3–5 | 3–5 |
| TF-300 | This fraction began to decompose at about 180° C. and remarkably decomposed above 195° C. | This spectrum has absorption bands in the vicinity of 3500–3300, 2920, 2850, 1660–1620, 1580–1540, 1460–1400, 1380–1360, 1120, 1080–1020, 970 and 820–800 $cm^{-1}$. | 38–47 | 5–7 | 1–4 |

TABLE 2-continued

| Fraction | Description | Spectrum | | | |
|---|---|---|---|---|---|
| TF-310 | This fraction began to decompose at about 180° C. and remarkably decomposed above 195° C. | This spectrum has absorption bands in the vicinity of 3500–3300, 2920, 2850, 1660–1620, 1580–1540, 1460–1400, 1380–1360, 1120, 1080–1020, 970 and 820–800 $cm^{-1}$. | 38–47 | 5–7 | 1–4 |
| TF-320 | This fraction began to decompose at about 180° C. and remarkably decomposed above 195° C. | This spectrum has absorption bands in the vicinity of 3500–3300, 2920, 2850, 1660–1620, 1580–1540, 1460–1400, 1380–1360, 1120, 1080–1020, 970 and 820–800 $cm^{-1}$. | 38–47 | 5–7 | 1–4 |
| TF-330 | This fraction began to decompose at about 180° C. and remarkably decomposed above 195° C. | This spectrum has absorption bands in the vicinity of 3500–3300, 2920, 2850, 1660–1620, 1580–1540, 1460–1400, 1380–1360, 1120, 1080–1020, 970 and 820–800 $cm^{-1}$. | 38–47 | 5–7 | 1–4 |
| TF-340 | This fraction began to decompose at about 140° C. and remarkably decomposed above 200° C. | This spectrum has absorption bands in the vicinity of 3500–3300, 2920, 2850, 1660–1640, 1580–1520, 1460–1440, 1410–1340, 1250–1220, 1120–1030, 970 and 835 $cm^{-1}$. | 32–34 | 4–6 | 3–5 |
| TF-350 | This fraction began to decompose at about 110° C. and remarkably decomposed above 180° C. | This spectrum has absorption bands in the vicinity of 3500–3300, 2920–2900, 1660–1630, 1580–1520, 1460–1340, 1140–1100, 1080–1020, 970 and 820–800 $cm^{-1}$. | 34–37 | 5–6 | 1–2 |

| | Properties Color reaction | | | | | |
|---|---|---|---|---|---|---|
| Fraction | Ninhydrin reaction | Molisch reaction | Phenol-$H_2SO_4$ reaction | Anthron-$H_2SO_4$ reaction | Indole-HCl reaction | Lowry-Folin reaction |
| TF-210 | | + | + | + | + | + |
| TF-220 | | + | + | + | + | + |
| TF-230 | | + | + | + | + | + |
| TF-240 | | + | + | + | + | + |
| TF-250 | | + | + | + | + | + |
| TF-300 | − | + | + | + | + | + |
| TF-310 | − | + | + | + | + | + |
| TF-320 | − | + | + | + | + | + |
| TF-330 | − | + | + | + | + | + |
| TF-340 | − | + | + | + | + | + |
| TF-350 | − | + | + | + | + | + |

| | Properties | | |
|---|---|---|---|
| Fraction | Ultraviolet absorption spectra (aqueous solution of pH of 7.0) $\lambda_{max}$ (nm) | Saccharide content in terms of glucose as measured by Phenol-$H_2SO_4$ method (%) | Protein content in terms of bovine serum alubumin as measured by Lowry-Folin's method (%) |
| TF-210 | At the absorption edge and in the vicinity of 248–265 nm* | ca. 5–ca. 25 | ca. 20–ca. 50 |
| TF-220 | At the absorption edge and in the vicinity of 248–266 nm* | ca. 5–ca. 20 | ≦ca. 10 |
| TF-230 | At the absorption edge and in the vicinity of 249–264 nm | ca. 5–ca. 25 | ca. 30–ca. 60 |
| TF-240 | At the absorption edge and in the vicinity of 250–265 nm | ca. 15–ca. 35 | ca. 20–ca. 30 |
| TF-250 | At the absorption edge and in the vicinity of 248–269 nm | ca. 60–ca. 80 | ca. 5–ca. 20 |
| TF-300 | At the absorption edge and in the vicinity of 246–280 nm | ca. 16–ca. 60 | ≦ca. 10 |
| TF-310 | At the absorption edge and in the vicinity of 246–280 nm | ″ | ″ |
| TF-320 | At the absorption edge and in the vicinity of 246–280 nm | ″ | ″ |
| TF-330 | At the absorption edge and in the vicinity of 246–280 nm | ca. 16–ca. 60 | ≦ca. 10 |
| TF-340 | At the absorption edge and in the vicinity of 246–280 nm | ca. 16–ca. 60 | ≦ca 10 |

TABLE 2-continued

| | | |
|---|---|---|
| TF-350 | At the absorption edge and in the vicinity of 245–264 nm | ca. 80–ca. 95 | $\leq$ca. 10 |

Note:
*Measurement was conducted on water-soluble fractions.

The pharmacological activities of the present carcinostatic substances TF-210, TF-220, TF-230, TF-240, TF-250, TF-300 (TF-310, TF-320, TF-330), TF-340 and TF-350 are as described below. In the following phamacological tests, the test substance TF-210 used was obtained in Example 1, TF-220 in Example 3, TF-230 in Example 5, TF-240 in Example 7, TF-250 in Example 9, TF-310-1 in Example 11 (1), TF-310-2 in Example 18, TF-320 in Example 12, TF-330 in Example 13, TF-340 in Example 19, TF-350 in Example 24, and TF-300 in Examples 11 to 18.

(1) Immunostimulating activity

Three ICR strain mice (female, 6 weeks old) were used for each group. Each of the test substances was dissolved in a physiological salt solution and 0.2 ml of each of the resulting solutions was intraperitoneally administered to the mice. Twenty four hours after the administration, 0.2 ml of a carbon suspension prepared by mixing 1 ml of Perikan Drawing Ink 17 Black (manufactured by Günther-Wagner Co., Ltd.) with 2 ml of a physiological salt solution containing 3% by weight of gelatin was intravenously injected into the mouse tail, and after 1, 5, 10 and 15 minutes from the injection, 0.02 ml of the blood was collected from the orbit by using a hematocrit capillary coated with heparin, and immediately diluted and hemolyzed with 1.6 ml of a 0.1% by weight aqueous sodium carbonate solution. This solution was subjected to colorimetry at 675 nm, and the phagocytotic index (K value) was determined from the equation of Halpern et al.

To the mice in the control groups was administered 0.2 ml of a physiological salt solution, $$K = \frac{\log C_0 - \log C}{t - t_0}$$

wherein $C_0$=carbon powder content in blood at the time of $t_0$, and C=carbon powder content in blood at the time of t.

The results are shown in Tables 3 to 5.

TABLE 3

| Substance | Dosage (mg/kg) | Average K value |
|---|---|---|
| TF-210 | 3 | 0.1155 ± 0.0273 |
| | 6 | 0.1198 ± 0.0231 |
| TF-220 | 1.5 | 0.1087 ± 0.0346 |
| | 3 | 0.1292 ± 0.0289 |
| TF-230 | 5 | 0.1028 ± 0.0175 |
| | 10 | 0.1194 ± 0.0334 |
| TF-240 | 5 | 0.1109 ± 0.0250 |

TABLE 3-continued

| Substance | Dosage (mg/kg) | Average K value |
|---|---|---|
| | 10 | 0.1127 ± 0.0496 |
| TF-250 | 5 | 0.0865 ± 0.0131 |
| | 10 | 0.1120 ± 0.0329 |
| Control | — | 0.0348 ± 0.0037 |

TABLE 4

| Substance | Dosage (mg/kg) | Average K value |
|---|---|---|
| *TF-310-1 | 0.1 | 0.0580 ± 0.0088 |
| | 1 | 0.0776 ± 0.0168 |
| TF-320 | 0.1 | 0.0468 ± 0.0123 |
| | 1 | 0.0715 ± 0.0040 |
| TF-330 | 0.1 | 0.0601 ± 0.0098 |
| | 1 | 0.0965 ± 0.0102 |
| Control | — | 0.0295 ± 0.0007 |

Note:
*The test was conducted on a group consisting of four mice.

TABLE 5

| Substance | Dosage (mg/kg) | Average K value |
|---|---|---|
| TF-340* | 5 | 0.1292 ± 0.0229 |
| | 10 | 0.1001 ± 0.0295 |
| TF-350 | 5 | 0.0817 ± 0.0002 |
| | 10 | 0.1453 ± 0.0229 |
| Control | — | 0.0408 ± 0.0016 |

Note:
*The test was conducted on a group consisting of 4 mice.

(2) Carcinotatic activity (i) Antitumor activity against Ehrlich ascites tumor

Ehrlich ascites tumor cells were intraperitoneally inoculated into ICR strain mice (female, 6 weeks old) in an amount of 1×10⁵ cells per mouse. Subsequently, each of the test substances was dissolved in a physiological salt solution and 0.2 ml of each of the resulting solutions was intraperitoneally administered to the mice once a day for seven consecutive days from the first day after the inoculation of the tumor cells. To the control groups, 0.2 ml of a physiological salt solution was administered in the same manner as above.

The results are shown in Tables 6 and 7.

$$T/C = \frac{\text{Survival days of the mice in a group to which the test substance was administered}}{\text{Survival days of the mice in the control group}} \times 100(\%)$$

TABLE 6

| Substance | Dosage (mg/kg × the number of administrations) | Average survival days (day) | T/C (%) | Ratio of survivors for 30 days | Ratio of complete cure |
|---|---|---|---|---|---|
| TF-210 | 0.7 × 7 | >27.2 ± 5.7 | >161 | 8/10 | 7/10 |
| | 3.5 × 7 | >26.8 ± 4.9 | >159 | 7/10 | 6/10 |
| TF-220 | 0.3 × 7 | >22.8 ± 6.1 | >135 | 2/8 | 1/8 |
| | 1.5 × 7 | >29.1 ± 2.3 | >173 | 7/8 | 5/8 |
| TF-230 | 1 × 7 | >29.9 ± 0.3 | >177 | 7/8 | 7/8 |
| | 5 × 7 | >28.3 ± 4.6 | >168 | 7/8 | 7/8 |

TABLE 6-continued

| Substance | Dosage (mg/kg × the number of administrations) | Average survival days (day) | T/C (%) | Ratio of survivors for 30 days | Ratio of complete cure |
| --- | --- | --- | --- | --- | --- |
| TF-240 | 1 × 7 | >23.2 ± 5.6 | >138 | 3/8 | 2/8 |
|  | 5 × 7 | >24.5 ± 7.5 | >146 | 5/8 | 5/8 |
| TF-250 | 1 × 7 | >20.3 ± 6.4 | >121 | 2/8 | 2/8 |
|  | 5 × 7 | >26.6 ± 5.5 | >158 | 5/8 | 5/8 |
| Control | — | 16.8 ± 2.6 | 100 | 0/8 | 0/8 |

TABLE 7

| Substance | Dosage (mg/kg × the number of administrations) | Average survival days (day) | T/C (%) | Ratio of survivors for 30 days | Ratio of complete cure |
| --- | --- | --- | --- | --- | --- |
| TF-310-1 | 0.1 × 7 | >27.9 ± 4.5 | >166 | 4/8 | 4/8 |
|  | 1 × 7 | >28.6 ± 2.3 | >170 | 6/8 | 6/8 |
| TF-320 | 0.5 × 7 | >29.0 ± 2.6 | >172 | 7/8 | 7/8 |
|  | 1 × 7 | >28.1 ± 4.9 | >167 | 7/8 | 7/8 |
| TF-330 | 0.5 × 7 | >29.8 ± 0.6 | >177 | 7/8 | 7/8 |
|  | 1 × 7 | >29.6 ± 0.9 | >176 | 7/8 | 7/8 |
| TF-340 | 1 × 7 | >28.3 ± 4.5 | >168 | 7/8 | 5/8 |
|  | 5 × 7 | >24.0 ± 9.4 | >143 | 5/8 | 5/8 |
| TF-350 | 1 × 7 | 19.6 ± 4.1 | 117 | 0/8 | 0/8 |
|  | 5 × 7 | >30.0 ± 0.0 | >179 | 8/8 | 8/8 |
| Control | — | 16.8 ± 2.3 | 100 | 0/8 | 0/8 |

(ii) Antitumor activity against Sarcoma-180 cells (a) Sarcoma-180 cells were intraperitoneally transplanted to ICR strain mice (female, 6 weeks old) in an amount of 1 × 10⁵ cells per mouse. Subsequently, each of the test substances was dissolved in a physiological salt solution and 0.2 ml of each of the resulting solutions was intraperitoneally administered to the mice once a day for seven consecutive days from the first day after the transplanting of the carcinoma cells. To the control group, 0.2 ml of a physiological salt solution was administered in the same manner as above. The results are shown in Table 8.

TABLE 8

| Substance | Dosage (mg/kg × the number of administrations) | Average survival days (day) | T/C (%) | Ratio of survivors for 30 days | Ratio of complete cure |
| --- | --- | --- | --- | --- | --- |
| TF-210 | 3.5 × 7 | >27.2 ± 5.6 | >183 | 4/5 | 4/5 |
|  | 7 × 7 | >30.0 ± 0.0 | >203 | 5/5 | 5/5 |
| TF-220 | 0.3 × 7 | >26.3 ± 6.0 | >177 | 2/5 | 2/5 |
|  | 1.5 × 7 | >30.0 ± 0.0 | >203 | 5/5 | 5/5 |
| TF-230 | 1 × 7 | >29.2 ± 1.6 | >197 | 4/5 | 4/5 |
|  | 5 × 7 | >24.8 ± 9.9 | >168 | 3/5 | 2/5 |
| TF-240 | 1 × 7 | >21.4 ± 7.3 | >145 | 2/5 | 1/5 |
|  | 5 × 7 | >30.0 ± 0.0 | >203 | 5/5 | 5/5 |
| TF-250 | 1 × 7 | >29.0 ± 2.0 | >196 | 4/5 | 4/5 |
|  | 5 × 7 | >28.4 ± 3.2 | >192 | 4/5 | 2/5 |
| Control | — | 14.8 ± 2.3 | 100 | 0/5 | 0/5 |

(b) Sarcoma 180 cells were subcutaneously transplanted at the armpit to ICR strain mice (female, 6 weeks old) in an amount of 1 × 10⁷ cells per mouse. Subsequently, each of the test substances was dissolved in a physiological salt solution or a 5% aqueous glucose solution and 0.2 ml of each of the resulting solution was intraveneously or intramuscularly administered to the mice once a day for seven consecutive days from the first day after the transplanting of the carcinoma cells. To the control groups, 0.2 ml of a 5% aqueous glucose solution or a physiological salt solution was administered in the same manner as above. The results are shown in Table 8-(2).

TABLE 8-(2)

| Substance | Route | Dose (mg/kg × the number of administrations) | Liquid in which substance was dissolved | Tumor weight (g) | T/C (%) |
| --- | --- | --- | --- | --- | --- |
| TF-310-1 | iv | 0.1 × 7 | Physiological salt solution | 0.29 ± 0.15 | 20 |
|  | im | 0.1 × 7 | Physiological salt solution | 0.86 ± 0.10 | 60 |
| Control | — | — | Physiological salt solution | 1.45 ± 0.31 | 100 |
| TF-320 | iv | 0.1 × 7 | Physiological salt solution | 1.54 ± 0.77 | 31 |
|  | im | 0.1 × 7 | Physiological salt solution | 3.50 ± 0.45 | 71 |
|  | iv | 0.1 × 7 | 5% aqueous glucose solution | 1.67 ± 0.58 | 34 |
|  | im | 0.1 × 7 | 5% aqueous glucose solution | 2.38 ± 0.42 | 48 |
| Control | — | — | 5% aqueous glucose solution | 4.94 ± 2.42 | 100 |
| TF-310-2 | iv | 0.001 × 7 | 5% aqueous glucose solution | 2.67 ± 0.20 | 51 |
|  |  | 0.005 × 7 | 5% aqueous glucose | 2.39 ± 0.56 | 46 |

TABLE 8-(2)-continued

| Substance | Route | Dose (mg/kg × the number of administrations) | Liquid in which substance was dissolved | Tumor weight (g) | T/C (%) |
|---|---|---|---|---|---|
| | | 0.01 × 7 | 5% aqueous glucose solution | 2.33 ± 0.26 | 44 |
| | | 0.05 × 7 | 5% aqueous glucose solution | 1.31 ± 0.26 | 25 |
| | | 0.1 × 7 | 5% aqueous glucose solution | 1.05 ± 0.21 | 20 |
| Control | — | | 5% aqueous glucose solution | 5.24 ± 0.49 | 100 |
| TF-310-2 | im | 0.1 × 7 | 5% aqueous glucose solution | 1.68 ± 0.30 | 36 |
| Control | — | | 5% aqueous glucose solution | 4.68 ± 0.57 | 100 |

The above data for TF-310-1 show the results on the 7th day after the transplating of Sarcoma 180 cells. The data for TF-320 and TF-310-2 show the results on the 14th day after the transplating of Sarcoma 180 cells.

(iii) Antitumor activity against Ehrlich solid tumor

Ehrlich tumor cells were subcutaneously transplanted at the armpit to ICR strain mice (female, 6 weeks old) in an amount of $4 \times 10^6$ cells per mouse. Subsequently, each of the test substances was dissolved in a physiological salt solution or a 5% aqueous glucose solution and 0.2 ml of each of the resulting solutions was intraperitoneally administered to the mice once a day for seven consecutive days from the first day after the transplanting of the tumor cells, or once in every other day for 10 days from the eighth day after the transplanting of the tumor cells. To the control groups, 0.2 ml of a physiological salt solution or a 5% aqueous glucose solution was administered in the same manner as above. The weight of each tumor was determined. The determination of the weight of the tumor was conducted by measuring the major diameter (a mm) and the minor diameter (b mm) by means of calipers, and substituting the values obtained for a and b in the following equation:

$$\text{Weight of tumor} = \frac{a \times b^2}{2} \text{ (mg)}$$

The results are shown in Tables 9-(1) and 9-(2).

TABLE 9-(1)

| Substance | Dosage (mg/kg × the number of administrations) | Administration day | Day 14* Tumor weight (g) | T/C (%) |
|---|---|---|---|---|
| TF-210 | 3.5 × 7 | Day 1, 2, 3, 4, 5, 6, 7 | 1.96 ± 0.7 | 29 |
| | 7 × 7 | | 2.62 ± 1.9 | 38 |
| TF-220 | 3 × 7 | | 4.30 ± 2.1 | 62 |
| | 6 × 7 | | 2.89 ± 1.2 | 42 |
| TF-230 | 10 × 7 | | 2.63 ± 1.22 | 38 |
| | 20 × 7 | | 2.04 ± 0.66 | 29 |
| TF-240 | 10 × 7 | | 4.07 ± 0.75 | 59 |
| | 20 × 7 | | 4.02 ± 1.66 | 59 |
| TF-250 | 10 × 7 | | 3.10 ± 1.01 | 46 |
| | 20 × 7 | | 3.19 ± 1.26 | 47 |
| Control | — | | 6.82 ± 1.14 | 100 |

TABLE 9-(2)

| Substance | Dosage (mg/kg × the number of administrations) | Administration day | Day 15** Tumor weight (g) | T/C (%) |
|---|---|---|---|---|
| TF-310-1 | 1 × 5 | Day 8, 10, 12, 14, 16 | 4.78 ± 2.01 | 55 |
| Control | — | | 8.70 ± 2.03 | 100 |

Note:
TF-210 to TF-250 were used after having been dissolved in a physiological salt solution. TF-310-1 was used in solution in a 5% aqueous glucose solution.
*, **The day when the weight of the tumor was measured.

(iv) Antitumor activity against B-16 melanoma cells (a) B-16 Melanoma cells were subcutaneously transplanted at the armpit to BDF$_1$ strain mice (male, 7 weeks old) in an amount of $1 \times 10^6$ cells per mouse. Subsequently, each of the test substances was dissolved in a physiological salt solution and 0.2 ml of each of the resulting solutions was intraperitoneally administered to the mice once a day for seven consecutive days from the first day after the transplanting of the tumor cells. To the control groups, 0.2 ml of a physiological salt solution was administered in the same manner as above. The weights of the tumors were determined on the 17th or 23rd day after the transplanting of the tumor cells. The determination method was the same as in above (iii). The results are shown in Table 10.

TABLE 10

| Substance | Dosage (mg/kg × the number of administrations) | Average tumor weight (g) | T/C (%) |
|---|---|---|---|
| TF-210 | 7 × 7 | 3.07 ± 0.7 | 64 |
| TF-220 | 1.5 × 7 | 3.92 ± 2.29 | 82 |
| | 3 × 7 | 3.69 ± 0.81 | 77 |
| TF-230 | 5 × 7 | 3.21 ± 0.64 | 67 |
| | 10 × 7 | 3.71 ± 1.08 | 77 |
| TF-240 | 5 × 7 | 3.78 ± 1.26 | 79 |
| | 10 × 7 | 4.00 ± 1.36 | 84 |
| TF-250 | 5 × 7 | 2.97 ± 0.73 | 62 |
| | 10 × 7 | 2.75 ± 0.67 | 58 |
| Control | — | 4.76 ± 0.68 | 100 |
| TF-310-1 | 3 × 7 | 2.53 ± 1.61 | 63 |
| Control | — | 4.00 ± 0.85 | 100 |

Note:
Average tumor weights for TF-210 to TF-250 were determined on the 17th day after the transplanting of the tumor cells.
Average tumor weight for TF-310-1 was determined on the 23rd day after the planting of the tumor cells.

(b) B-16 Melanoma cells were subcutaneously transplanted at the armpit to BDF$_1$ strain mice (male, 6 weeks old) in an amount of $1 \times 10^6$ cells per mouse. Subsequently, the test substance was dissolved in a 5% aqueous glucose solution and 0.2 ml of the resulting solution was administered simultaneously intratumorously and intraperitoneally once in every other day for 12 days from the 13th day after the transplanting of the tumor cells. To the control group, each 0.2 ml of a 5% aqueous glucose solution was administered in the same manner as above. The results are shown in Table 10-(2).

TABLE 10-(2)

| Substance | Dosage mg/kg × the number of administrations | Route | Tumor weight (g) | T/C (%) |
|---|---|---|---|---|
| TF-310-2 | 1.0 × 6 | it | 2.92 ± 0.23 | 50 |
| | 5.0 × 6 | | 4.08 ± 0.72 | 70 |
| | 10.0 × 6 | | 3.26 ± 0.26 | 56 |
| | 0.5 × 6 | it | 4.31 ± 0.24 | 74 |

TABLE 10-(2)-continued

| Sub-stance | Dosage mg/kg × the number of admini-strations) | Route | Tumor weight (g) | T/C (%) |
|---|---|---|---|---|
|  | 1.0 × 6 | +ip | 1.92 ± 0.38 | 33 |
| Control | — |  | 5.83 ± 0.80 | 100 |

The tumor weight was measured on 23rd day.

(3) Acute toxicity $LD_{50}$ values for mice (ICR strain, female, 6 weeks old, intravenous administration) are shown in Table 12.

TABLE 12

| Substance | $LD_{50}$ (mg/kg) |
|---|---|
| TF-210 | >100 |
| TF-220 | >200 |
| TF-230 | >100 |
| TF-240 | >200 |
| TF-250 | >200 |
| TF-300 | >10 |
| TF-340 | >200 |
| TF-350 | >200 |

As is evident from the above-mentioned pharmacological experiments, the TF-2 substances of this invention are useful as carcinostatic agents, can be expected to have activities against various cancerous diseases, and can be expected to have remarkable activities against particularly solid cancers. All the TF-2 substances of this invention have excellent effects.

The TF-2 substances of this invention may be used after shaping them into various pharmaceutical forms such as oral drugs, injections, suppositories or the like, though they are used preferably in the pharmaceutical form of an injection. When they are used as oral drugs, the oral drugs may contain various excipients, and may be formed into capsules, tablets, powder, or granules. When they are used as injections, the injections may be any of subcutaneous injections, intramuscular injections, and intravenous injections, and they are used in the form of a suspension, a solution or a powder which is dissolved in a saline solution or the solution containing a glucose or a local anesthetics when used.

The dosage of the TF-2 substances (TF-210, 220, 230, 240, 250, 300 (310, 320, 330), 340 and 350) of this invention is properly selected depending on the conditions of a patient, though in general, it is desirable to administer them in a dosage for an adult of 0.005 to 50 mg/kg once a day or several times a day, and as to the administration method, they are administered preferably by subcutaneous, intramuscular, or intravenous injection or injection into the affected part.

This invention is further explained in detail below referring to Examples and the accompanying drawings, in which drawings, FIG. 1 shows a microscopic photograph indicating the form of *Fusobacterium nucleatum* TF-031 used in this invention;

FIG. 20 shows a high performance liquid chromatogram of said substance;

FIG. 21 shows an infrared absorption spectrum of the carcinostatic substance TF-330 (purified) obtained in Example 13, which appears hereinafter;

EXAMPLE 1

Figure 1:
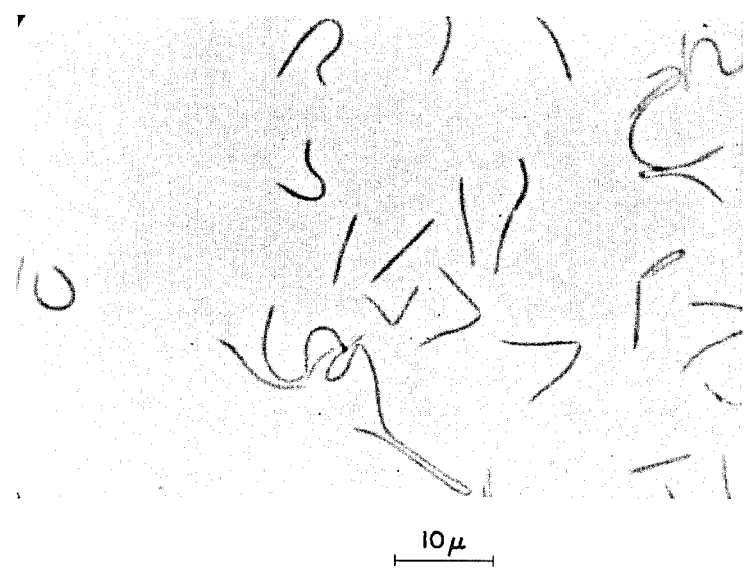

(1) In a 10-liter jar fermenter (manufactured by Marubishi Rika Kenkyusho) was placed 8 liters of a TF-e culture medium containing 17 g of trypticase peptone, 10 g of heart infusion, 3 g of yeast extract, 7.5 g of sodium chloride, 12 g of glucose, 10 g of lactose, 0.1 g of sodium sulfite and 0.5 g of sodium thioglycolate, per liter of distilled water. The culture medium was sterilized for 30 min. at 120° C. After cooling the culture medium, nitrogen gas was passed through the same at a rate of 100 ml/min for 1 hr. Into this culture medium was inoculated 1 liter of a preculture solution of *Fusobacterium nucleatum* TF-031 (FERM-5077, ATCC-31647) previously prepared by culturing it in a TF-e culture medium having the same composition as above. The cells were cultured for 3 days at 37° C. with stirring (30 r.p.m.) while introducing nitrogen gas at a rate of 65 ml/min. After the culturing, to the culture were added 160 g of Celite and 80 g of cellulose powder and the mixture was stirred and filtered under reduced pressure to obtain 7.8 liters of a bacteria-free supernatant fluid of the culture.

(2) To 7.8 liters of the above supernatant fluid was added 117 ml of concentrated hydrochloric acid to adjust the pH of the supernatant fluid to 2.0, after which 11.7 liters of ethanol was added thereto to form a 60% aqueous ethanol solution, which was then allowed to stand for 24 hours at 4° C. Subsequently, the supernatant fluid was removed by decantation and the remaining portion was subjected to centrifugation ($6 \times 10^3$ r.p.m., 5 min.) at 4° C. to collect the precipitate. This precipitate was washed with 400 ml of a 60% aqueous solution having a pH of 2.0, 400 ml of ethanol, 200 ml of acetone and 200 ml of diethyl ether in this order, and dried under reduced pressure to obtain 3.9 g of powder.

(3) The powder obtained in above (2) was suspended in 25 ml of water. The pH of the resulting suspension was adjusted to 7.5 to 8.0 by adding 1N aqueous sodium hydroxide solution, and after stirring for 30 min at room temperature, 1N hydrochloric acid was added thereto to adjust the pH thereof to 4.0. Subsequently, after stirring for 2 hours with ice-cooling, the mixture was subjected to centrifugation ($1 \times 10^4$ r.p.m., 10 min) to separate the precipitate from the supernatant fluid. This precipitate was washed with 10 ml of water having a pH of 4.0, and the precipitate was separated from the washing by centrifugation ($1 \times 10^4$ r.p.m., 10 min). The washing and the above supernatant fluid were combined and subjected to the treatment described in Example 9. The precipitate was washed with 10 ml of ethanol and dried under reduced pressure to obtain 1.5 g of the carcinostatic substance TF-210.

Figure 2:
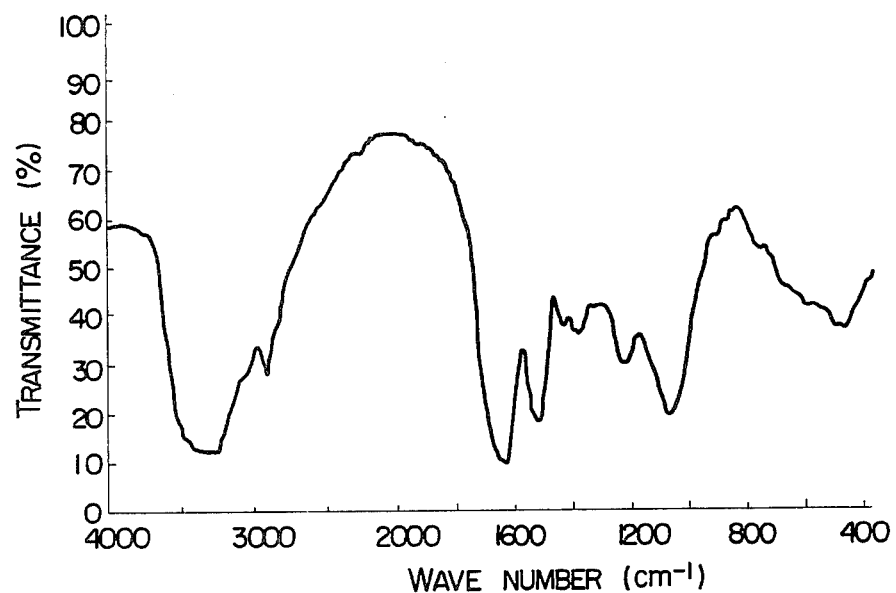
FIG. 2 shows an infrared absorption spectrum of the carcinostatic substance TF-210 obtained in Example 1, which appears hereinafter.
Figure 3:
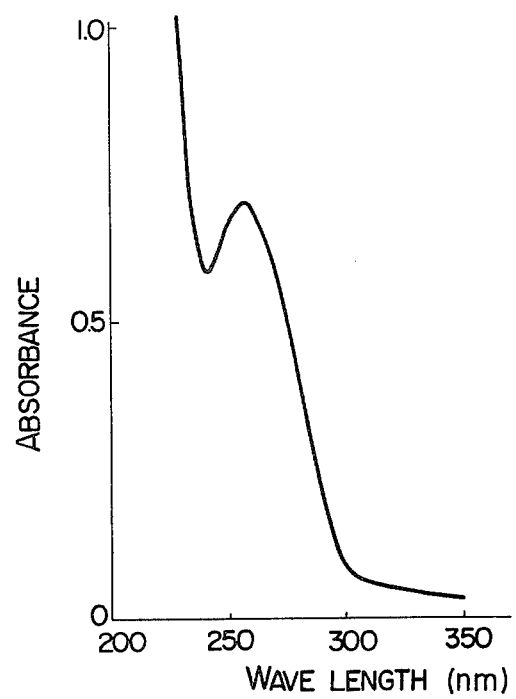
FIG. 3 shows an ultraviolet absorption spectrum of said substance.

The thus obtained carcinostatic substance TF-210 had the properties shown in Table 2. The infrared absorption spectrum and ultraviolet absorption spectrum thereof are shown in FIGS. 2 and 3, respectively.

EXAMPLE 2

(1) In a 10-liter jar fermenter was placed 8 liters of a TF-d culture medium containing 17 g of trypticase peptone, 20 g of heart infusion, 3 g of yeast extract, 7.5 g of sodium chloride, 12 g of glucose, 10 g of lactose, 0.1 g of sodium sulfite and 0.5 g of sodium thioglycolate per liter of distilled water. The culture medium was sterilized for 30 min at 120° C. After cooling of the culture medium, nitrogen gas was passed through the same for 1 hour at a rate of 100 ml/min. Into this culture medium was inoculated 1 liter of a preculture solution of *Fusobacterium nucleatum* TF-031 (FERM-5077, ATCC-31647) previously prepared by culturing it in a TF-d culture medium having the same composition as above. The cells were cultured for 3 days at 37° C. with stirring (30 r.p.m.) while introducing nitrogen gas at a rate of 65 ml/min. After the culturing, to the culture solution were added 160 g of Celite and 80 g of cellulose powder, and the resulting mixture was stirred and filtered under reduced pressure to obtain 7.8 liters of a bacteria-free supernatant fluid of the culture.

(2) To 7.8 liters of the supernatant fluid obtained in above (1) was added 117 ml of concentrated hydrochloric acid to adjust the pH of the supernatant fluid to 2.0. Then, 11.7 liters of ethanol was added to the supernatant fluid to form a 60% aqueous ethanol solution, which was then allowed to stand for 24 hours at 4° C. Subsequently, the supernatant fluid was removed by decantation, and the remaining portion was subjected to centrifugation ($6 \times 10^3$ r.p.m., 5 min) at 4° C. to collect the precipitate. This precipitate was washed with 400 ml of a 60% aqueous ethanol solution having a pH of 2.0, 400 ml of ethanol, 200 ml of acetone and 200 ml of diethyl ether in this order, and dried under reduced pressure to obtain 4.5 g of powder.

(3) This powder was subjected to the same treatment as in Example 1 (3) to obtain 1.6 g of the carcinostatic substance TF-120.

The thus obtained carcinostatic substance TF-210 had the properties shown in Table 2. The infrared absorption spectrum and ultraviolet absorption spectrum thereof were substantially identical with those obtained in Example 1.

EXAMPLE 3

(1) In a 10-liter jar fermenter was placed 8 liters of a TF-e culture medium having the same composition as in Example 1. The culture medium was sterilized for 30 min at 120° C. After cooling of the culture medium, nitrogen gas was passed through the same for 1 hour at a rate of 100 ml/min. Into this culture medium was inoculated 1 liter of a preculture solution of *Fusobacterium nucleatum* TF-031 (FERM-5077, ATCC-31647) previously prepared by culturing it in a TF-e culture medium having the same composition as above. The cells were cultured for 5 days at 37° C. with stirring (30 r.p.m.) while introducing nitrogen gas at a rate of 65 ml/min. After the culturing, to the culture medium were added 160 g of Celite and 80 g of cellulose powder, and the resulting mixture was stirred and filtered under reduced pressure to obtain 7.8 liters of a bacteria-free supernatant fluid of the culture solution.

(2) To 7.8 liters of the supernatant fluid obtained in above (1) was added 117 ml of concentrated hydrochloric acid to adjust the pH of the supernatant fluid to 2.0. Then, 11.7 liters of ethanol was added to the supernatant fluid to form a 60% aqueous ethanol solution, which was then allowed to stand at 4° C. for 24 hours. Subsequently, the supernatant fluid was removed by decantation and the remaining portion was subjected to centrifugation ($6 \times 10^3$ r.p.m., 5 min) at 4° C. to collect the precipitate. This precipitate was washed with 400 ml of a 60% aqueous ethanol solution having a pH of 2.0, 400 ml of ethanol, 200 ml of acetone, and 200 ml of diethyl ether in this order, and dried under reduced pressure to obtain 4.9 g of powder.

(3) The powder obtained in above (2) was suspended in 49 ml of water. The pH of the resulting suspension was adjusted to 7.5 to 8.0 by adding 1N aqueous sodium hydroxide solution, and after stirring for 30 min at room temperature, the pH of the suspension was adjusted to 6.0 by adding 1N hydrochloric acid. Subsequently, the suspension was stirred with ice cooling for 2 hours after which the mixture was subjected to centrifugation ($1 \times 10^4$ r.p.m., 10 min) to separate the precipitate from the supernatant fluid. This precipitate was washed with 5 ml of water having a pH of 6.0, and the precipitate was separated from the washing by centrifugation ($1 \times 10^4$ r.p.m., 10 min). The precipitate was washed with 10 ml of ethanol and dried under reduced pressure to obtain 1.8 g of the carcinostatic substance TF-220.

Figure 4:
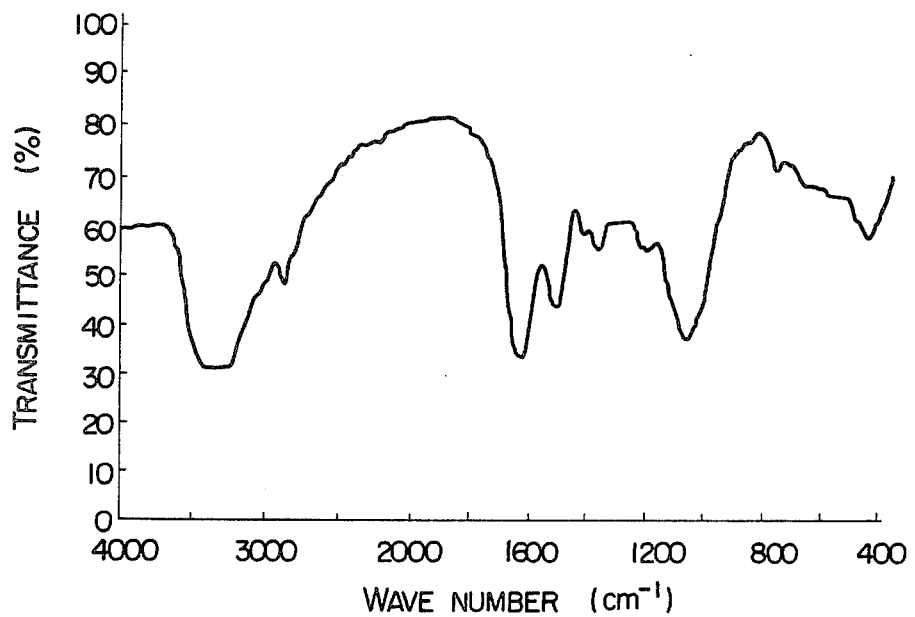
FIG. 4 shows an infrared absorption spectrum of the carcinostatic substance TF-220 obtained in Example 3, which appears hereinafter.
Figure 5:
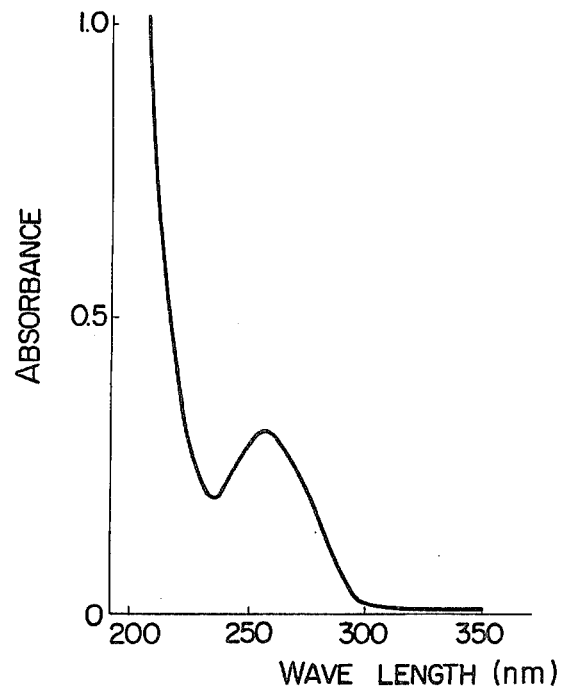
FIG. 5 shows an ultraviolet absorption spectrum of said substance.

The thus obtained carcinostatic substance THF-220 had the properties shown in Table 2. The infrared absorption spectrum and ultraviolet absorption spectrum thereof are shown in FIGS. 4 and 5, respectively.

EXAMPLE 4

(1) In a 10-liter jar fermenter was placed 8 liters of a TF-d culture medium having the same composition as in Example 2. The culture medium was sterilized for 30 min at 120° C. After cooling of the culture medium, nitrogen gas was passed through the same for 1 hour at a rate of 100 ml/min. Into this culture medium was inoculated 1 liter of a preculture solution of *Fusobacterium nucleatum* TF-031 (FERM-5077, ATCC-31647) previously prepared by culturing it in a TF-d culture medium having the same composition as above. The cells were cultured for 5 days at 37° C. with stirring (30 r.p.m.) while introducing nitrogen gas at a rate of 65 ml/min. After the culturing, to the culture solution were added 160 g of Celite and 80 g of cellulose powder, and the resulting mixture was stirred and filtered under reduced pressure to obtain 7.8 liters of a bacteria-free supernatant fluid of the culture.

(2) To 7.8 liters of the above supernatant fluid was added 117 ml of concentrated hydrochloric acid to adjust the pH of the supernatant fluid to 2.0. Then, 11.7 liters of ethanol was added to the supernatant fluid to form a 60% aqueous ethanol solution, which was then allowed to stand at 4° C. for 24 hours. Subsequently, the solution portion was removed by decantation, and the remaining portion was subjected to centrifugation ($6 \times 10^3$ r.p.m., 5 min) at 4° C. to collect the precipitate. This precipitate was washed with 400 ml of a 60% aqueous ethanol solution having a pH of 2.0, 400 ml of ethanol, 200 ml of acetone and 200 ml of diethyl ether in this order, and dried under reduced pressure to obtain 5.07 g of powder.

(3) The powder thus obtained was treated in the same manner as in Example 3 (3), to obtain 1.9 g of the carcinostatic substance TF-220.

The thus obtained carcinostatic substance TF-220 had the properties shown in Table 2. The infrared absorption spectrum and ultraviolet radiation absorption spectrum thereof were substantially identical with those obtained in Example 3.

EXAMPLE 5

(1) In a 10-liter jar fermenter was placed 8 liters of a TF-e culture medium having the same composition as in Example 1. The culture medium was sterilized for 30 min at 120° C. After cooling of the culture medium, nitrogen gas was passed through the same for 1 hour at a rate of 100 ml/min. Into this culture medium was inoculated 1 liter of a preculture solution of *Fusobacterium nucleatum* TF-031 (FERM-5077, ATCC-31647) previously prepared by culturing it in a TF-e culture medium having the same composition as above. The cells were cultured for 2 days at 37° C. with stirring (30 r.p.m.) while introducing nitrogen gas at a rate of 65 ml/min. After the culturing, to the culture solution were added 160 g of Celite and 80 g of cellulose powder, and the resulting mixture was stirred and filtered under reduced pressure to obtain 7.8 liters of a bacteria-free supernatant fluid of the culture.

(2) To 7.8 liters of the supernatant fluid obtained in above (1) was added 117 ml of concentrated hydrochloric acid to adjust the pH of the same to 2.0. Then, 11.7 liters of ethanol was added to the supernatant fluid to form a 60% aqueous ethanol solution, which was then allowed to stand at 4° C. for 24 hours until the precipitate had been completely settled. Subsequently, the supernatant fluid was removed by decantation, and the remaining portion was subjected to centrifugation ($6 \times 10^3$ r.p.m., 5 min) at 4° C. to collect the precipitate. This precipitate was washed with 400 ml of a 60% aqueous ethanol solution having a pH of 2.0, 400 ml of ethanol, 200 ml of acetone and 200 ml of diethyl ether in this order, and dried under reduced pressure to obtain 2.73 g of powder.

(3) The powder obtained in above (2) was suspended in 25 ml of water. The pH of the resulting suspension was adjusted to 7.5 to 8.0 by adding 1N aqueous sodium hydroxide solution, and the suspension was stirred at room temperature for 30 min, after which 1N hydrochloric acid was added thereto to adjust the pH to 6.0. Subsequently, the suspension was stirred with ice cooling for 2 hours, and thereafter subjected to centrifugation ($1 \times 10^4$ r.p.m., 10 min) to separate the precipitate from the supernatant fluid. This precipitate was washed with 5 ml of water having a pH of 6.0, and the precipitate was separated from the washing by centrifugation ($1 \times 10^4$ r.p.m., 10 min). The washing and the above supernatant fluid were combined and the resulting solution, after having been adjusted to a pH of 4.0 by adding 1N hydrochloric acid, was allowed to stand at a temperature of not more than 5° C. for 12 hours, and subsequently subjected to centrifugation ($1 \times 10^4$ r.p.m., 10 min) to separate the precipitate from the supernatant fluid. This precipitate was washed with 15 ml of water having a pH of 4.0, and the precipitate was separated from the washing by centrifugation ($1 \times 10^4$ r.p.m., 10 min), and the precipitate was washed with 10 ml of ethanol and then dried under reduced pressure to obtain 0.58 g of the carcinostatic substance TF-230.

Figure 6:
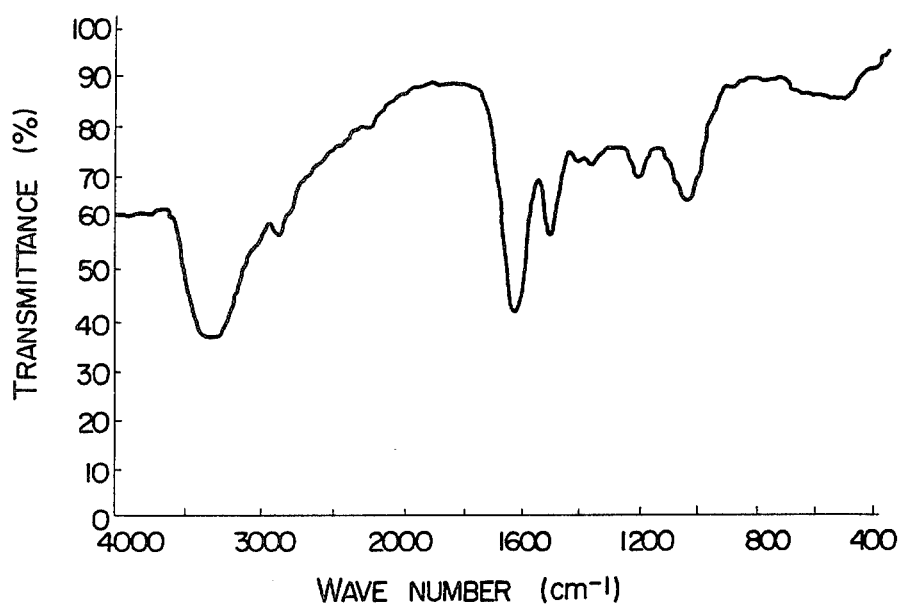
FIG. 6 shows an infrared absorption spectrum of the carcinostatic substance TF-230 obtained in Example 5, which appears hereinafter.
Figure 7:
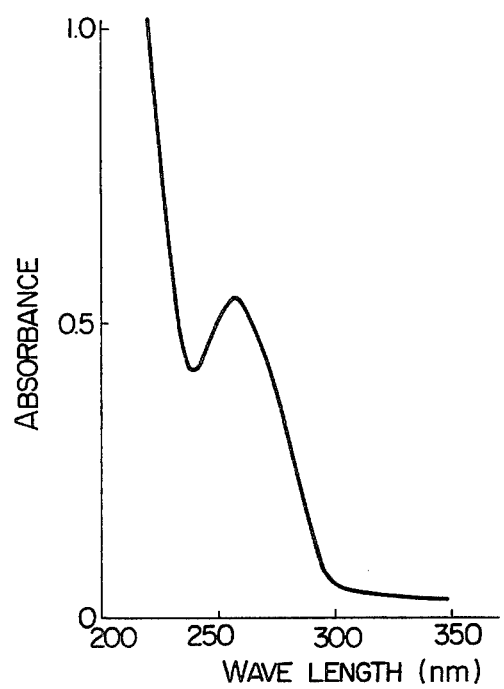
FIG. 7 shows an ultraviolet absorption spectrum of said substance.

The thus obtained carcinostatic substance TF-230 had the properties shown in Table 2. The infrared absorption spectrum and ultraviolet absorption spectrum thereof are shown in FIGS. 6 and 7, respectively.

EXAMPLE 6

(1) In a 10-liter jar fermenter was placed 8 liters of a TF-d culture medium having the same composition as in Example 2. The culture medium was sterilized for 30 min at 120° C. After cooling of the culture medium, nitrogen gas was passed through the same for 1 hour at a rate of 100 ml/min. Into this culture medium was inoculated 1 liter of a preculture solution of *Fusobacterium nucleatum* TF-031 (FERM-5077, ATCC-31647) previously prepared by culturing it in a culture medium having the same composition as above. The cells were cultured for 2 days at 37° C. with stirring (30 r.p.m.) while introducing nitrogen gas at a rate of 65 ml/min. After the cultureing, to the culture solution were added 160 g of Celite and 80 g of cellulose powder, and the resulting mixture was stirred and filtered under reduced pressure to obtain 7.8 liters of a bacteria-free supernatant fluid of the culture.

(2) To 7.8 liters of the supernatant fluid obtained in above (1) was added 117 ml of concentrated hydrochloric acid to adjust the pH of the supernatant fluid to 2.0. Then, 11.7 liters of ethanol was added to the supernatant fluid to form a 60% aqueous ethanol solution, which was then allowed to stand at 4° C. for 24 hours. Subsequently, the supernatant fluid was removed by decantation and the remaining portion was subjected to centrifugation ($6\times10^3$ r.p.m., 5 min) at 4° C. to collect the precipitate. This precipitate was washed with 400 ml of a 60% aqueous ethanol solution having a pH of 2.0, 400 ml of ethanol, 200 ml of acetone and 200 ml of diethyl ether in this order, and dried under reduced pressure to obtain 3.15 g of powder.

(3) The powder obtained in above (2) was treated in the same manner as in Example 5 (3) to obtain 0.8 g of the carcinostatic substance TF-230. The thus obtained carcinostatic substance TF-230 had the properties shown in Table 2. The infrared absorption spectrum and ultraviolet absorption spectrum thereof were substantially identical with those obtained in Example 5.

EXAMPLE 7

(1) In 25 ml of water was suspended 3.9 g of the powder obtained in the same manner as in Example 1 (1) and (2). By adding 1N aqueous sodium hydroxide solution, the pH of the resulting suspension was adjusted to 7.5 to 8.0, and after stirring the suspension at room temperature for 30 min, the pH was again adjusted to 6.0 by adding 1N hydrochloric acid. After stirring for 2 hours with ice-cooling, the suspension was subjected to centrifugation ($1\times10^4$ r.p.m., 10 min) to separate the precipitate from the supernatant fluid. This precipitate was washed with 5 ml of water having a pH of 6.0 and the precipitate was separated from the washing by centrifugation ($1\times10^4$ r.p.m., 10 min). This washing and the above supernatant fluid were combined and subjected to the treatment described in (2) appearing below. The precipitate was washed with 10 ml of ethanol and dried under reduced pressure to obtain 1.06 g of the carcinostatic substance TF-220.

The thus obtained carcinostatic substance TF-220 had the properties shown in Table 2. The infrared absorption spectrum and ultraviolet absorption spectrum thereof were substantially identical with those obtained in Example 3.

(2) To the combined solution consisting of the supernatant fluid and the washing obtained in above (1) was added 1N hydrochloric acid to adjust the pH to 4.0, and then the mixture was allowed to stand for 12 hours at not more than 5° C. Subsequently, the mixture was subjected to centrifugation ($1\times10^4$ r.p.m., 10 min) to separate the precipitate from the supernatant fluid. This precipitate was washed with 5 ml of water having a pH of 4.0, and the precipitate and the washing were subjected to centrifugation ($1\times10^4$ r.p.m., 10 min). The washing was combined with the above supernatant fluid and the combined solution was subjected to the treatment described in (3) appearing below. The precipitate was washed with 5 ml of ethanol and dried under reduced pressure to obtain 0.48 g of the carcinostatic substance TF-230.

The thus obtained carcinostatic substance TF-230 had the properties shown in Table 2. The infrared absorption spectrum and ultraviolet absorption spectrum thereof were substantially identical with those obtained in Example 5.

(3) To the combined solution consisting of the supernatant fluid and the washing obtained in above (2) was added 1N hydrochloric acid to adjust the pH to 2.0, and the mixture was allowed to stand for 2 hours with ice-cooling. The mixture was subjected to centrifugation ($6\times10^3$ r.p.m., 10 min) to separate the precipitate from the supernatant fluid. This precipitate was washed with 3 ml of water having a pH of 2.0, and the precipitate and the washing were subjected to centrifugation ($6\times10^3$ r.p.m., 10 min). The washing was combined with the above supernatant fluid and the combined solution was subjected to the treatment described in (4) appearing below. The precipitate was washed with 5 ml of ethanol and dried under reduced pressure to obtain 0.10 g of the carcinostatic substance TF-240.

Figure 8:
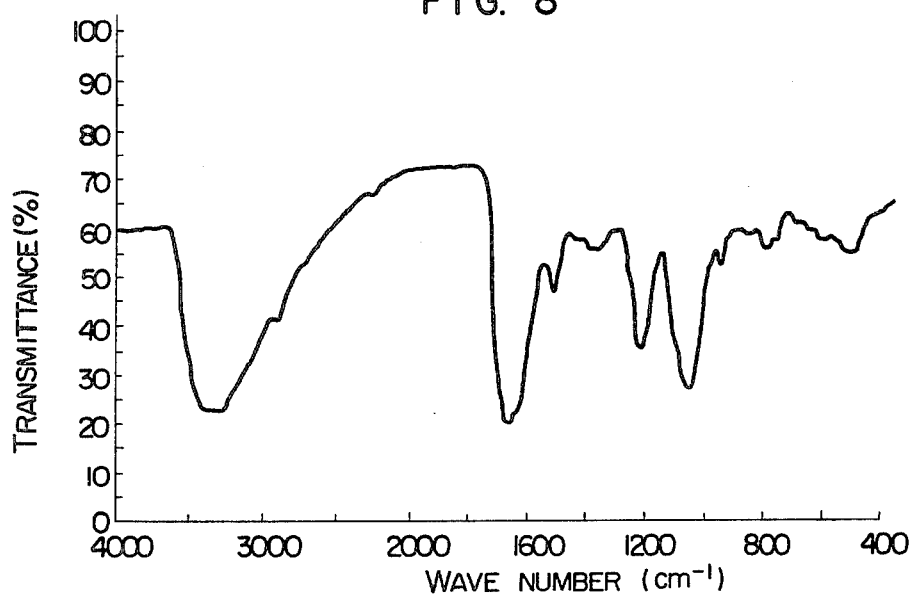
FIG. 8 shows an infrared absorption spectrum of the carcinostatic substance TF-240 obtained in Example 7, which appears hereinafter.
Figure 9:
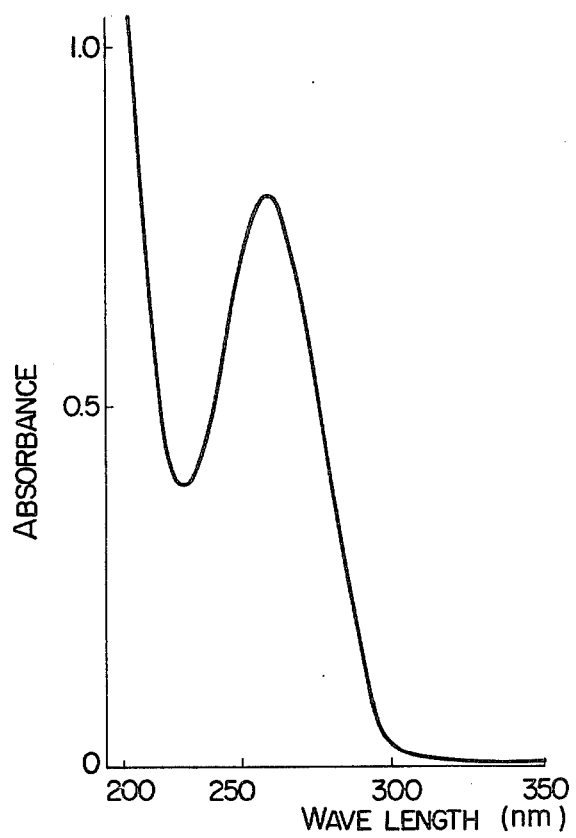
FIG. 9 shows an ultraviolet absorption spectrum of said substance.

The thus obtained carcinostatic substance TF-240 had the properties shown in Table 2. The infrared absorption spectrum and ultraviolet absorption spectrum thereof are shown in FIGS. 8 and 9, respectively.

(4) Ethanol was added to the combined solution consisting of the supernatant fluid and the washing obtained in above (3) to form an 80% aqueous ethanol solution, and the aqueous ethanol solution was allowed to stand at not more than 5° C. for 12 hours. The substance deposited was removed by centrifugation ($6\times10^3$ r.p.m., 10 min) and the deposit was washed with 10 ml of an 80% aqueous ethanol solution and 10 ml of ethanol in this order, and dried under reduced pressure to obtain 2.08 g of the carcinostatic substance TF-250.

The thus obtained carcinostatic substance TF-250 had the properties shown in Table 2. The infrared absorption spectrum and ultraviolet absorption spectrum thereof were substantially identical with those obtained in Example 9 hereinafter.

EXAMPLE 8

In 45 ml of water was suspended 4.5 g of a powder obtained in the same manner as in Example 2 (1) and (2). By adding 1N aqueous sodium hydroxide solution, the pH of the resulting suspension was adjusted to 7.5 to 8.0, and after stirring at room temperature for 30 min, was again adjusted to 4.0 by adding 1N hydrochloric acid. The suspension was subjected to centrifugation ($1\times10^4$ r.p.m., 10 min) to separate the precipitate from the supernatant fluid. This precipitate was washed with 5 ml of water having a pH of 4.0 and the precipitate and the washing were subjected to centrifugation ($1\times10^4$ r.p.m., 10 min). This washing and the above supernatant fluid were combined, and the pH of the combined solution was adjusted to 2.0 by adding 1N hydrochloric acid, after which the solution was allowed to stand for 2 hours while cooling it with ice water, and then subjected to centrifugation ($6\times10^3$ r.p.m., 10 min) to separate the resulting precipitate from the supernatant fluid. The precipitate separated was washed with 3 ml of water having a pH of 2.0, and the precipitate and the washing were subjected to centrifugation ($6\times10^3$ r.p.m., 10 min). The precipitate obtained was washed with 5 ml of ethanol and dried under reduced pressure to obtain 0.12 g of the carcinostatic substance TF-240.

The thus obtained carcinostatic substance TF-240 had the properties shown in Table 2. The infrared absorption spectrum and ultraviolet absorption spectrum thereof were substantially identical with those obtained in Example 7.

EXAMPLE 9

(1) To the combined solution consisting of the supernatant fluid and the washing obtained in Example 1 (3) was added 1N hydrochloric acid to adjust the pH to 2.0, and then the mixture was allowed to stand for 2 hours with ice-cooling. Subsequently, the mixture was subjected to centrifugation ($6 \times 10^3$ r.p.m., 10 min) to separate the precipitate from the sueprnatant fluid. This precipitate was washed with 3 ml of water having a pH of 2.0, and the precipitate and the washing were subjected to centrifugation ($6 \times 10^3$ r.p.m., 10 min). The washing was combined with the above supernatant fluid and the combined solution was subjected to a treatment described in (2) appearing below. The precipitate was washed with 5 ml of ethanol and dried under reduced pressure to obtain 0.11 g of the carcinostatic substance TF-240.

The thus obtained carcinostatic substance TF-240 had the properties shown in Table 2. The infrared absorption spectrum and ultraviolet absorption spectrum were substantially identical with those obtained in Example 7.

(2) Ethanol was added to the combined solution consisting of the supernatant fluid and the washing obtained in above (1) to form an 80% aqueous ethanol solution, and the ethanol solution was allowed to stand for 12 hours at not more than 5° C. The substance deposited was removed by centrifugation ($6 \times 10^3$ r.p.m., 10 min) and the deposit was washed with 10 ml of an 80% aqueous ethanol solution and 10 ml of ethanol in this order, and dried under reduced pressure to obtain 2.1 g of the carcinostatic substance TF-250.

Figure 10:
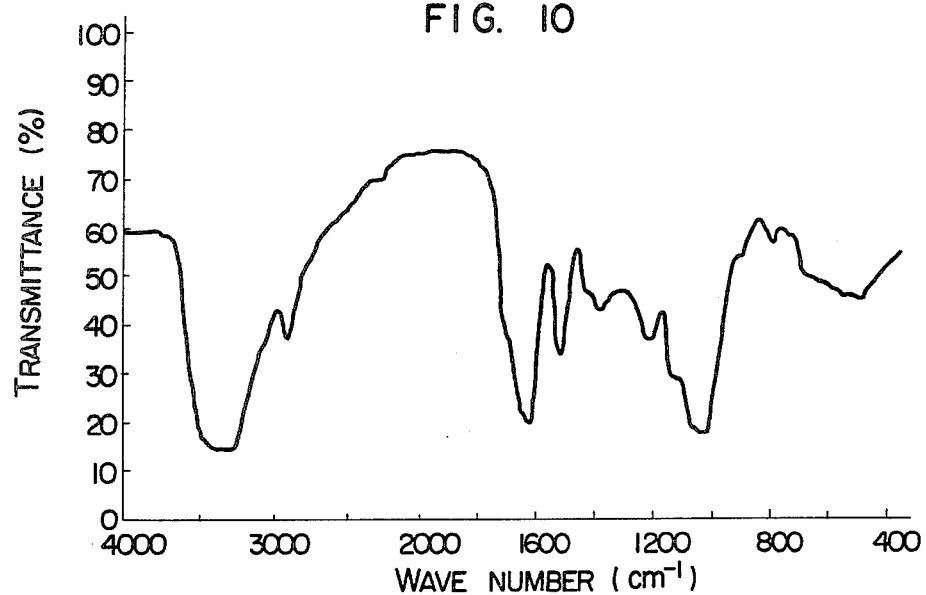
FIG. 10 shows an infrared absorption spectrum of the carcinostatic substance TF-250 obtained in Example 9, which appears hereinafter.
Figure 11:
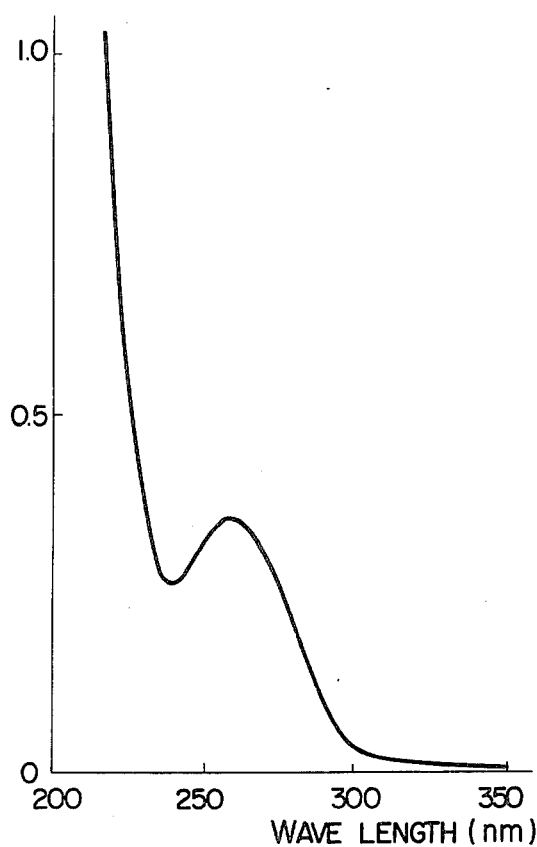
FIG. 11 shows an ultraviolet absorption spectrum of said substance.

The thus obtained carcinostatic substance TF-250 had the properties shown in Table 2. The infrared absorption spectrum and ultraviolet absorption spectrum thereof are shown in FIGS. 10 and 11, respectively.

EXAMPLE 10

In 45 ml of water was suspended 4.5 g of a powder obtained in the same manner as in Example 2 (1) and (2). By adding 1N aqueous sodium hydroxide solution, the pH of the resulting suspension was adjusted to 7.5 to 8.0, and after stirring at room temperature for 30 min, was again adjusted to 2.0 by adding 1N hydrochloric acid. The mixture was subjected to centrifugation ($6 \times 10^3$ r.p.m., 10 min) to separate the precipitate from the supernatant fluid. This precipitate was washed with 10 ml of water having a pH of 2.0, and the precipitate and the washing were subjected to centrifugation ($6 \times 10^3$ r.p.m., 10 min). This washing and the above supernatant fluid were combined, and ethanol was added to this solution to form an 80% aqueous ethanol solution. The solution was allowed to stand for 12 hours at not more than 5° C., and then subjected to centrifugation ($6 \times 10^3$ r.p.m., 10 min) to obtain the deposit. The deposit separated was washed with 10 ml of an 80% aqueous ethanol solution and 10 ml of ethanol in this order, and dried under reduced pressure to obtain 2.68 g of the carcinostatic substance TF-250.

The thus obtained carcinostatic substance TF-250 had the properties shown in Table 2. The infrared absorption spectrum and ultraviolet absorption spectrum thereof were substantially identical with those obtained in Example 9.

EXAMPLE 11

(1) In 15 ml of water was suspended 1.5 g of the carcinostatic substance TF-210 obtained in Example 1. To the resulting suspension was added 1N aqueous sodium hydroxide solution with stirring, to adjust the pH of the suspension to 7.8. The suspension was heated to 37° C. and thereto were added 15 mg of Pronase E (trade name of Kaken Kagaku; 1,000,000 tyrosine units/g) and several drops of toluene. With shaking, the mixture was subjected to enzyme treatment at a pH of 7.8 to 8.0 at 37° to 40° C. for 24 hours. After the treatment, the mixture was subjected to centrifugation (4,000 r.p.m., 10 min) to separate the precipitate from the supernatant fluid. To the precipitate was added 3 ml of water having a pH of 8.0 and the mixture was subjected to centrifugation (4,000 r.p.m., 10 min) to separate the precipitate from the washing. This washing and the above supernatant fluid were combined and 1N hydrochloric acid was added thereto to adjust the pH to 2.0, upon which a precipitate is formed. This mixture was allowed to stand at 5° C. for 12 hours and then subjected to centrifugation ($1 \times 10^4$ r.p.m., 10 min) to separate the precipitate from the supernatant fluid. To the precipitate was added 3 ml of water having a pH of 2.0, and the mixture was subjected to centrifugation ($1 \times 10^4$ r.p.m., 10 min) to separate the precipitate from the washing. This washing and the above supernatant fluid were combined, and ethanol was added to this solution to form an 80% aqueous ethanol solution. The aqueous ethanol solution was stirred for 2 hours with ice-cooling and then subjected to centrifugation (4,000 r.p.m., 10 min) to separate the precipitate from the supernatant fluid. The precipitate was washed with 5 ml of an 80% aqueous ethanol solution and 5 ml of ethanol in this order, and then dried under reduced pressure to obtain 327 mg of the carcinostatic substance TF-310 fraction.

In 5 ml of water was dissolved 327 mg of the above powder, and the pH of the resulting solution was adjusted to 7.0 by adding 1N aqueous sodium hydroxide solution. The solution thus prepared was poured into a column packed with 45 ml of Amberlite IRA 400 (trade name of Rohm and Haas) preadjusted to the OH type with 1N aqueous sodium hydroxide solution. Subsequently, 200 ml of water was passed through the column. All the eluates were combined and the pH thereof was adjusted to 7.0 by adding 1N hydrochloric acid. This solution was concentrated under reduced pressure and then filtered through a Millipore filter having a pore diameter of 0.3 μm (Millipore: trade name of Japan Millipore Limited) and finally freeze-dried to obtain 210 mg of the freeze-dried carcinostatic substance TF-310.

Figure 12:
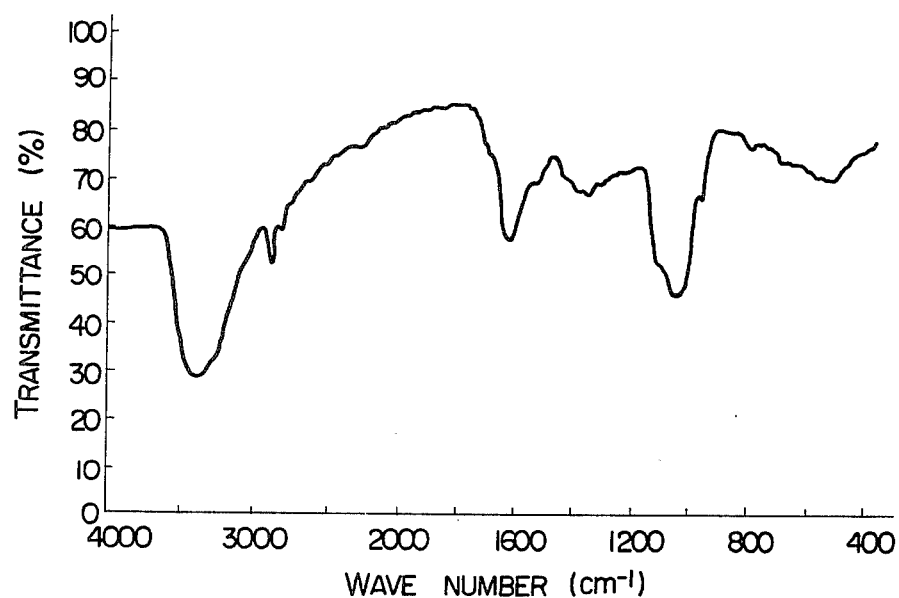
FIG. 12 shows an infrared absorption spectrum of the carcinostatic substance TF-310 obtained in Example 11, which appears hereinafter.
Figure 13:
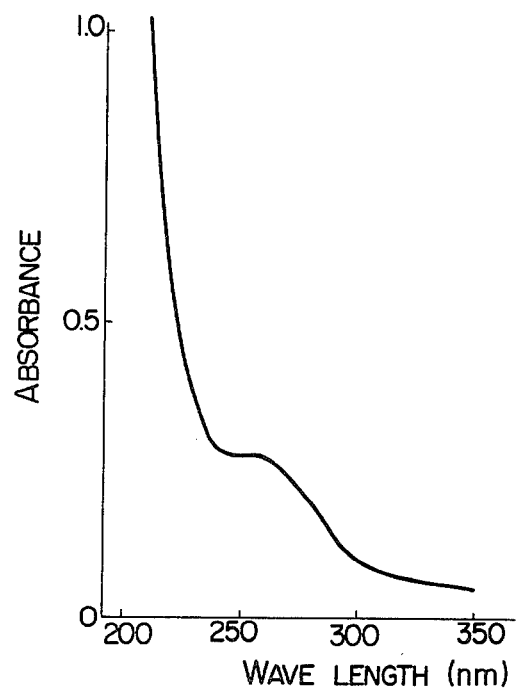
FIG. 13 shows an ultraviolet absorption spectrum of said substance.
Figure 14:
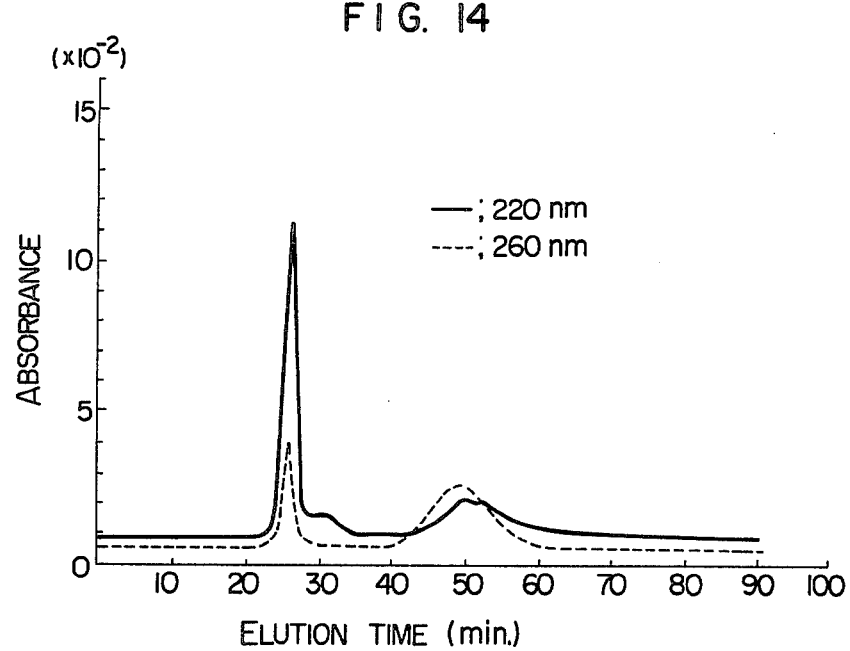
FIG. 14 shows a high performance liquid chromatogram of said substance.

The thus obtained carcinostatic substance TF-310 had the properties shown in Table 2 and the saccharide content thereof was generally about 20 to 60% in terms of glucose. The infrared absorption spectrum, ultraviolet absorption spectrum and high performance liquid chromatogram of a typical one are shown in FIGS. 12, 13 and 14, respectively.

(2) In 50 ml of water was dissolved 140 mg of the carcinostatic substance TF-310 obtained above, and the resulting solution was concentrated to a concentration 100 times the initial one by the use of Ultrafilter UK-50 (trade name for ultrafilter membrane of Toyo Roshi Kabushiki Kaisha, nominal molecular weight cutoff: 50,000). This concentrate was filtered through a Millipore filter having a pore diameter of 0.2 μm and then freeze-dried to obtain 88 mg of the purified, freeze-dried carcinostatic substance TF-310. The purified carcinostatic substance TF-310 thus obtained had the properties shown in Table 2 and the saccharide content thereof was generally about 16 to 30% in terms of glucose.

EXAMPLE 12

(1) In 10 ml of water was suspended 1 g of the carcinostatic substance TF-220 obtained in the same manner as in Example 7 (1). To the resulting suspension was added 1N aqueous sodium hydroxide solution with stirring to adjust the pH thereof to 7.8. The mixture was heated to 37° C., and thereto were added 15 mg of Pronase E and several drops of toluene. With shaking, the mixture was subjected to enzyme treatment at a pH of 7.8 to 8.0 at 37° to 40° C. for 24 hours. After the treatment, the mixture was subjected to centrifugation (4,000 r.p.m., 10 min) to separate the precipitate from the supernatant fluid. To the precipitate was added 3 ml of water having a pH of 8.0 and the mixture was subjected to centrifugation (4,000 r.p.m., 10 min) to separate the precipitate from the washing. This washing and the above supernatant fluid were combined and to the solution was added 1N hydrochloric acid to adjust to the pH to 2.0, upon which a precipitate was formed. This mixture was allowed to stand at 5° C. for 12 hours and then subjected to centrifugation ($1\times10^4$ r.p.m., 10 min) to separate the precipitate from the supernatant fluid. To the precipitate was added 3 ml of water having a pH of 2.0 and the mixture was subjected to centrifugation ($1\times10^4$ r.p.m., 10 min) to separate the precipitate from the washing. This washing and the above supernatant fluid were combined and ethanol was added to this solution to form an 80% aqueous ethanol solution. The aqueous ethanol solution was stirred for 2 hours with ice-cooling and then subjected to centrifugation (4,000 r.p.m., 10 min) to separate the precipitate from the supernatant fluid. The precipitate was washed with 5 ml of an 80% aqueous ethanol solution, and 5 ml of ethanol in this order, and then dried under reduced pressure to obtain 163 mg of the carcinostatic substance TF-320 fraction.

In 5 ml of water was dissolved 150 mg of the above powder and the resulting solution was adjusted to a pH of 7.0 by adding 1N aqueous sodium hydroxide solution. The solution thus prepared was poured into a column packed with 25 ml of Amberlite IRA 400 preadjusted to the OH type with 1N aqueous sodium hydroxide solution. Subsequently, 100 ml of water was passed through the column. All the eluates were combined, and 1N hydrochloric acid was added thereto to adjust the pH thereof to 7.0. This solution was concentrated under reduced pressure and then filtered through a Millipore filter having a pore diameter of 0.3 μm, and finally freeze-dried to obtain 110 mg of the freeze-dried carcinostatic substance TF-320.

Figure 15:
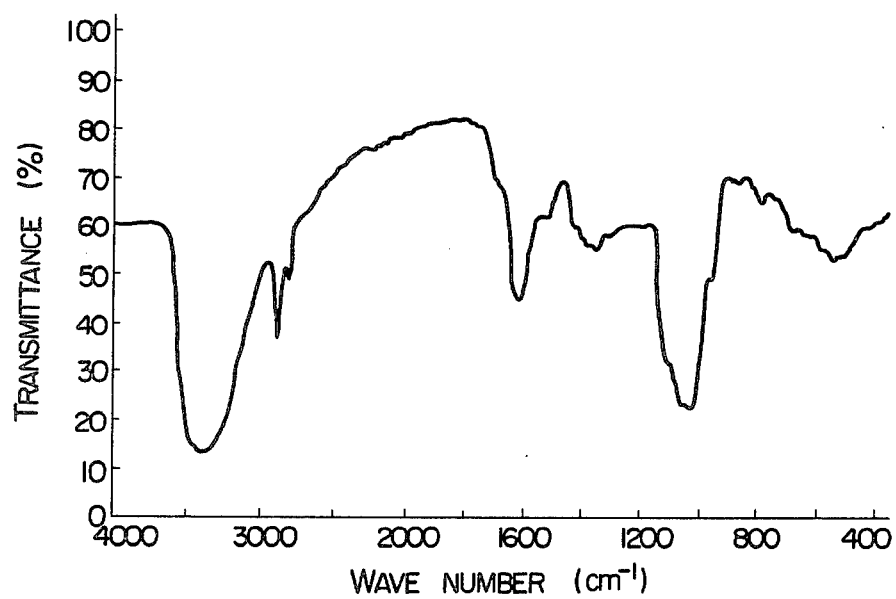
FIG. 15 shows an infrared absorption spectrum of the carcinostatic substance TF-320 obtained in Example 12, which appears hereinafter.
Figure 16:
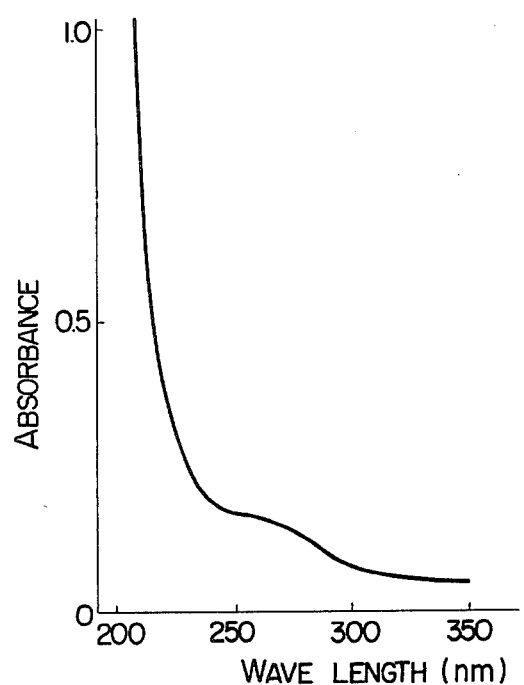
FIG. 16 shows an ultraviolet absorption spectrum of said substance.
Figure 17:
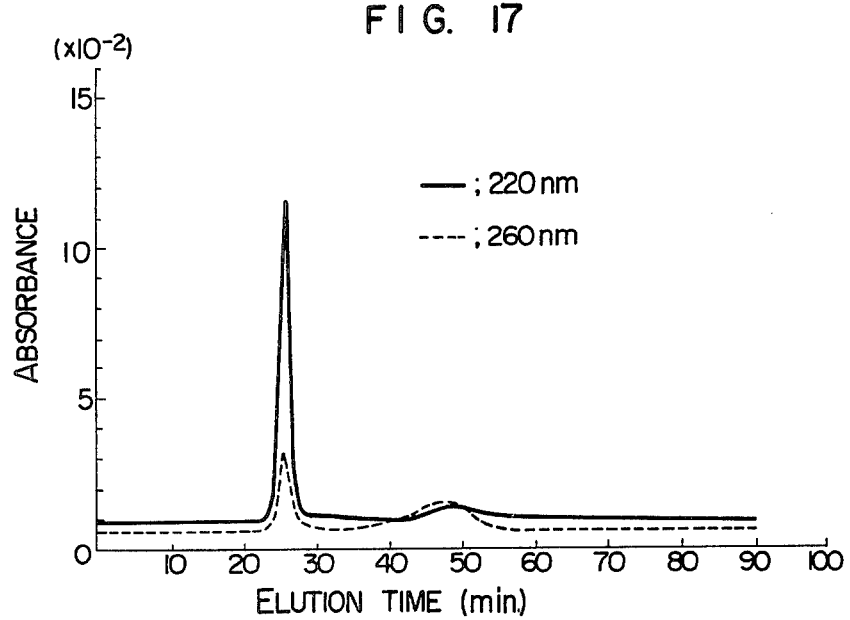
FIG. 17 shows a high performance liquid chromatogram of said substance.

The thus obtained carcinostatic substance TF-320 had the properties shown in Table 2 and the saccharide content thereof was generally about 20 to 60% in terms of glucose. The infrared absorption spectrum, ultraviolet absorption spectrum and high performance liquid chromatogram of a typical one are shown in FIGS. 15, 16 and 17, respectively.

(2) In 50 ml of water was dissolved 100 mg of the carcinostatic substance TF-320 obtained above, and the resulting solution was concentrated to a concentration 100 times the initial one by the use of Ultrafilter UK-50. This concentrate was filtered through a Millipore filter having a pore diameter of 0.2 μm, and then freeze-dried to obtain 72 mg of the purified, freeze-dried carcinostatic substance TF-320. The purified carcinostatic substance TF-320 thus obtained had the properties shown in Table 2 and the saccharide content thereof was generally about 16 to 30% in terms of glucose.

EXAMPLE 13

(1) In 5 ml of water was suspended 0.48 g of the carcinostatic substance TF-230 obtained in the same manner as in Example 7 (2). To the suspension was added 1N aqueous sodium hydroxide solution with stirring to adjust the pH to 7.8. The mixture was heated to 37° C. and thereto were added 5.0 mg of Pronase E, and several drops of toluene. With shaking, the mixture was subjected to enzyme treatment at a pH of 7.8 to 8.0 at 37° to 40° C. for 24 hours. After the treatment, the mixture was subjected to centrifugation (4,000 r.p.m., 10 min) to separate the precipitate from the supernatant fluid. To the precipitate was added 3 ml of water having a pH of 8.0, and the mixture was subjected to centrifugation (4,000 r.p.m., 10 min) to separate the precipitate from the washing. This washing and the above supernatant fluid were combined and to the solution was added 1N hydrochloric acid to adjust the pH to 2.0, upon which a precipitate was formed. This mixture was allowed to stand at 5° C. for 12 hours, and then subjected to centrifugation ($1\times10^4$ r.p.m., 10 min) to separate the precipitate from the supernatant fluid. To the precipitate was added 3 ml of water having a pH of 2.0, and the mixture was subjected to centrifugation ($1\times10^4$ r.p.m., 10 min) to separate the precipitate from the washing. This washing and the above supernatant fluid were combined and ethanol was added to this solution to form an 80% aqueous ethanol solution. The aqueous ethanol solution was stirred for 2 hours with ice-cooling and then subjected to. centrifugation (4,000 r.p.m., 10 min) to separate the precipitate from the supernatant fluid. The precipitate was washed with 5 ml of an 80% aqueous ethanol solution and 5 ml of ethanol in this order, and then dried under reduced pressure to obtain 100 mg of the carcinostatic substance TF-330 fraction.

In 5 ml of water was dissolved 100 mg of the above powder and the pH of the resulting solution was adjusted to 7.0 by adding 1N aqueous sodium hydroxide solution. The solution thus prepared was poured into a column packed with 15 ml of Amberlite IRA 400 preadjusted to the OH type with 1N aqueous sodium hydroxide solution. Subsequently, 60 ml of water was passed through the column. All the eluates were combined and adjusted to a pH of 7.0 by adding 1N hydrochloric acid. This solution was concentrated under reduced pressure and then filtered through a Millipore filter having a pore diameter of 0.3 μm and finally freeze-dried to obtain 70 mg of the freeze-dried carcinostatic substance TF-330.

Figure 18:
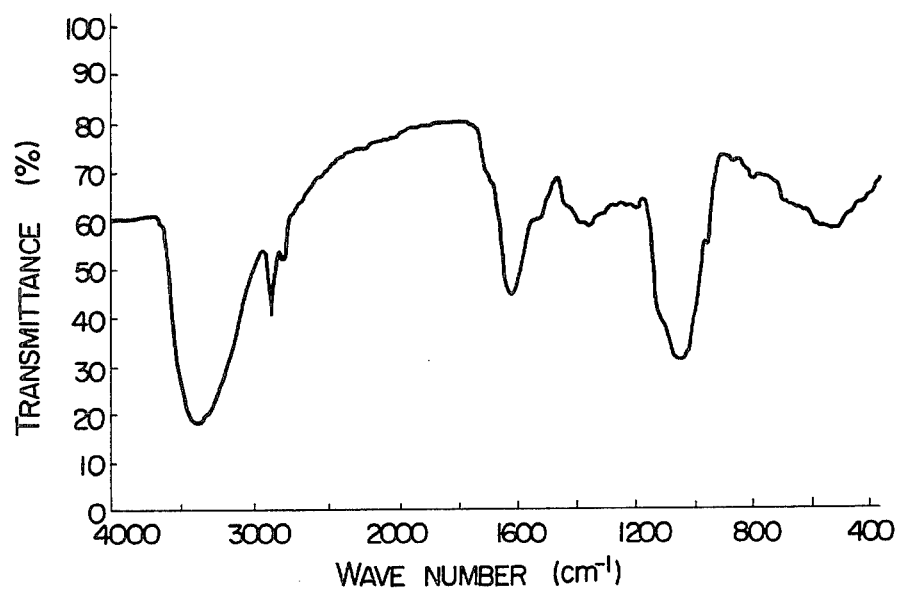
FIG. 18 shows an infrared absorption spectrum of the carcinostatic substance TF-330 obtained in Example 13, which appear hereinafter.
Figure 19:
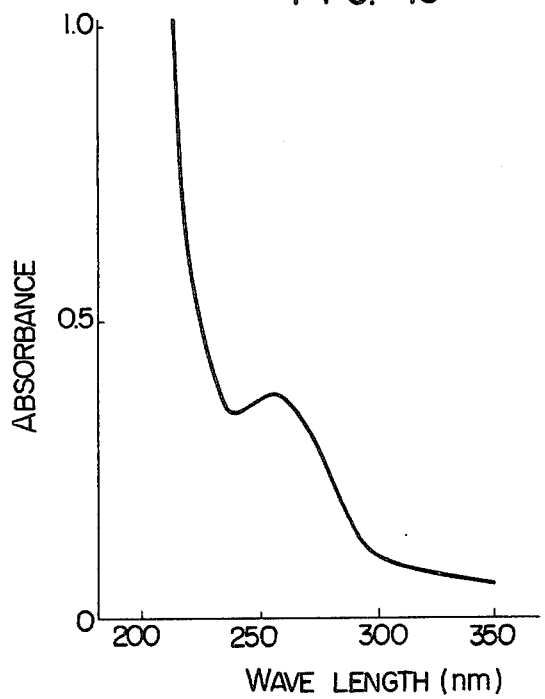
FIG. 19 shows an ultraviolet absorption spectrum of said substance.

The thus obtained carcinostatic substance TF-330 had the properties shown in Table 2. The infrared absorption spectrum, ultraviolet absorption spectrum and high performance liquid chromatogram of a typical one are shown in FIGS. 18, 19 and 20, respectively.

Figure 22:
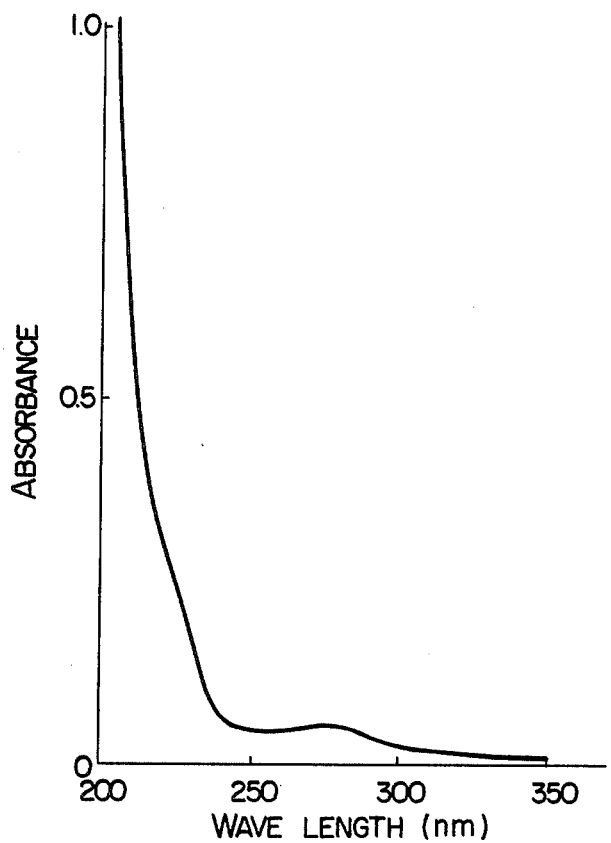
FIG. 22 shows an ultraviolet absorption spectrum of said substance.

(2) In 50 ml of water was dissolved 70 mg of the carcinostatic substance TF-330 obtained above, and the resulting solution was concentrated to a concentration 100 times the initial one by the use of Ultrafilter UK-50. This concentrate was filtered through a Millipore filter having a pore diameter of 0.2 μm, and then freeze-dried to obtain 49 mg of the purified, freeze-dried carcinostatic substance TF-330. The purified carcinostatic substance TF-330 thus obtained had the properties shown in Table 2 and the saccharide content thereof was generally about 16 to 30% in terms of glucose. The infrared absorption spectrum and ultraviolet absorption spectrum of a typical TF-330 are shown in FIGS. 21 and 22, respectively.

EXAMPLE 14

(1) In the same manner as in Example 2 (3), 7 (1) or 7 (2), there was treated 4.5 g of the substance obtained in the same manner as in Example 2 (1) and (2), to obtain the carcinostatic substance TF-210, TF-220 or TF-230, respectively.

(2) The carcinostatic substances TF-210, TF-220 or TF-230 obtained in (1) was treated in the same manner as in Example 11 (1), Example 12 (1) or Example 13 (1), to obtain the freeze-dried carcinostatic substance TF-310, TF-320 or TF-330 in a quantity of 220, 120 or 75 mg, respectively.

The thus obtained carcinostatic substances TF-310, TF-320 and TF-330 had the properties shown in Table 2 and the infrared absorption spectra, ultraviolet absorption spectra and high performance liquid chromatograms thereof were substantially identical with those obtained in Examples 11, 12 and 13, respectively.

EXAMPLE 15

In the same manner as in Example 11, there was treated 1.5 g of the carcinostatic substance TF-210 obtained in Example 1, except that (a) 15 mg of trypsin (manufactured by Difco) was used in place of Pronase E in the enzyme treatment and (b) a 60% aqueous ethanol solution was prepared in place of the 80% aqueous ethanol solution when the precipitate was collected from the water-soluble portion having a pH of 2 after the enzyme treatment. Thus, 200 mg of the freeze-dried, carcinostatic substance TF-310 was obtained.

Similarly, the following freeze-dried carcinostatic substances TF-320 and TF-330 were obtained.

| Carcinostatic substance | Trypsin | Freeze-dried carcinostatic substance |
|---|---|---|
| TF-220   1 g | 15 mg | TF-320 100 mg |
| TF-23.0 0.48 g | 5 mg | TF-330  65 mg |

The above obtained carcinostatic substances TF-310, TF-320 and TF-330 had the properties shown in Table 2, and the infrared absorption spectra, ultraviolet absorption spectra and high performance liquid chromatograms were substantially identical with those obtained in Examples 11, 12 and 13 (1), respectively.

EXAMPLE 16

The carcinostatic substances TF-210, TF-220 or TF-230 obtained in Example 1, Example 7 (1) or Example 7 (2), respectively, was treated in the same manner as in Example 11 (1), Example 12 (1) or Example 13 (1), respectively, except that, after the enzyme treatment, a 60% aqueous ethanol solution was prepared in place of the 80% aqueous ethanol solution when the precipitate was collected from the water-soluble portion having a pH of 2.0. Thus, the freeze-dried carcinostatic substances TF-310, TF-320 and TF-330 were obtained in quantities of 190, 98 and 66 mg, respectively.

The thus obtained carcinostatic substances TF-310, TF-320 and TF-330 had the properties shown in Table 2, and the infrared absorption spectra, ultraviolet absorption spectra and high performance liquid chromatograms were substantially identical with those obtained in Examples 11, 12 and 13 (1), respectively.

EXAMPLE 17

The carcinostatic substances TF-210, TF-220 or TF-230 obtained in Example 1, Example 7 (1) or Example 7 (2), respectively, was treated in the same manner as in Example 11 (1), Example 12 (1) or Example 13 (1), respectively, except that, after the enzyme treatment, in collecting the precipitate from the water-soluble portion having a pH of 2.0, a 60% aqueous ethanol solution was formed in place of the 80% aqueous ethanol solution, and subjected to the same subsequent treatment as in the respective Examples, to obtain 192 mg, 102 mg or 65 mg of the freeze-dried carcinostatic substances TF-310, TF-320 or TF-330, respectively.

The thus obtained carcinostatic substances TF-310, TF-320 and TF-330 had the properties shown in Table 2, and the infrared absorption spectra, ultraviolet absorption spectra and high performance liquid chromatograms were substantially identical with those obtained in Examples 11, 12 and 13 (1), respectively.

EXAMPLE 18

In a 90-liter jar fermenter (MSJ-$U_2$ type, manufactured by Marubishi Rika Kenkyusho) was placed a TF-f culture medium prepared by adding to 70 liters of distilled water 1190 g of trypticase peptone, 1050 g of heart infusion, 210 g of yeast extract, 525 g of sodium chloride, 840 g of glucose, 700 g of lactose, 7 g of sodium sulfite, 35 g of sodium thioglycolate and 175 g of potassium secondary phosphate. The culture medium was sterilized at 118° C. for 15 min. After cooling, nitrogen gas was passed through the medium at a rate of 250 ml/min for 1 hour.

Into this culture medium was inoculated about 900 ml of a precultured solution of Fusobacterium nucleatum TF-031 (FERM-5077, ATCC-31647) previously prepared by preculturing in a TF-f culture having the same composition as above. The cells were cultured for 4 days at about 33° C. with stirring (90 r.p.m.) while introducing nitrogen gas at a rate of 250 ml/min. After the culturing, to the culture solution were added 10 g/liter of Celite and 5 g/liter of cellulose powder and the mixture was stirred and filtered under reduced pressure to obtain about 65 liters of a bacteria-free supernatant fluid of the culture.

(2) To 7.5 liters of the above supernatant fluid was added 113 ml of concentrated hydrochloric acid to adjust the pH of the supernatant fluid to 2.0. Then, 11.4 liters of ethanol was added to the supernatant fluid to form a 60% aqueous ethanol solution, which was then allowed to stand at 4° C. for 24 hours. Subsequently, the solution portion was removed by decantation and the remaining portion was subjected to centrifugation ($4 \times 10^3$ r.p.m., 10 min) at 4° C. to collect the precipitate. This precipitate was washed with two 100-ml portions of a 60% aqueous ethanol solution having a pH of 2.0, with one 150-ml portion of ethanol, with one 150-ml portion of methanol and finally with one 150-ml portion of acetone in this order, and air-dried to obtain 3.0 g of powder.

(3) The powder obtained in above (2) was suspended in 30 ml of water. The pH of the resulting suspension was adjusted to 7.5 to 8.0 by adding 4N aqueous sodium hydroxide solution, and after stirring at room temperature for 15 min, was again adjusted to 4.0 by adding 4N hydrochloric acid. Subsequently, the suspension was allowed to stand with ice-cooling for 2 hours, the mixture was subjected centrifugation (1×10⁴ r.p.m., 10 min) to separate the precipitate from the supernatant fluid. To the precipitate separated was added 6 ml of water for washing, by which a suspension was formed, to which 4N aqueous sodium hydroxide solution was added to adjust the pH to 7.5 to 8.0. The suspension was stirred at room temperature for 15 min, after which 4N hydrochloric acid was added to the suspension to adjust the pH to 4.0, and the suspension was allowed to stand for 2 hours with ice-cooling. Then, the suspension was subjected to centrifugation (1×10⁴ r.p.m., 10 min) to collect the precipitate. This precipitate was washed with 4 ml of water having a pH of 4.0 and subjected to centrifugation (1×10⁴ r.p.m., 10 min) to obtain 6.2 g (wet weight) of a precipitate (TF-210).

The thus obtained carcinostatic substance TF-210 had the properties shown in Table 2 and the infrared absorption spectrum and ultraviolet absorption spectrum thereof were substantially identical with those obtained in Example 1.

(4) The precipitate (6.2 g (wet weight)) obtained in above (3) was suspended in 6 ml of water. To the suspension was added, with stirring, a saturated aqueous ammonium carbonate solution to adjust the pH of the suspension to 7.8. The suspension was heated to 37° C. and thereto were added 21 mg of Pronase E and then several drops of toluene. The resulting mixture was subjected, with shaking, to enzyme treatment at a pH of 7.8 to 8.0 at 37° to 40° C. for 24 hours. The pH of the thus treated mixture was adjusted to 1.0 by adding 4N hydrochloric acid, upon which a precipitate was formed. This suspension was allowed to stand for 2 hours with ice-cooling, and then subjected to centrifugation (1×10⁴ r.p.m., 10 min) to collect the supernatant fluid. To the supernatant fluid was added 29 ml of ethanol to form a 60% aqueous ethanol solution, upon which a precipitate was formed. This slurry was allowed to stand for 2 hours with ice-cooling and then subjected to centrifugation (6×10³ r.p.m., 10 min) to collect the precipitate. The precipitate collected was washed with 5 ml of a 60% aqueous ethanol solution, 10 ml of ethanol and 10 ml of acetone in this order, and air-dried to obtain 315 mg of crude crystals of the carcinostatic substance TF-310.

The crude crystals (315 mg) was dissolved in 30 ml of water, and 4N aqueous sodium hydroxide solution was added thereto to adjust the pH to 8.0. The resulting solution was poured into a column packed with 30 ml of Dowex 1×4 (trade name of Dow Chemical) Cl type. Subsequently, 100 ml of water was passed through the column and all the eluates were combined, adjusted to a pH of 6.5 to 7.0, and filtered through Ultrafilter UK-50 after which the filtrate was concentrated to a concentration 100 times the initial one. This concentrate was filtered through a Millipore filter having a pore diameter of 0.3 μm, and then freeze-dried to obtain 230 mg of the freezed-dried, purified carcinostatic substance TF-310.

Figure 23:
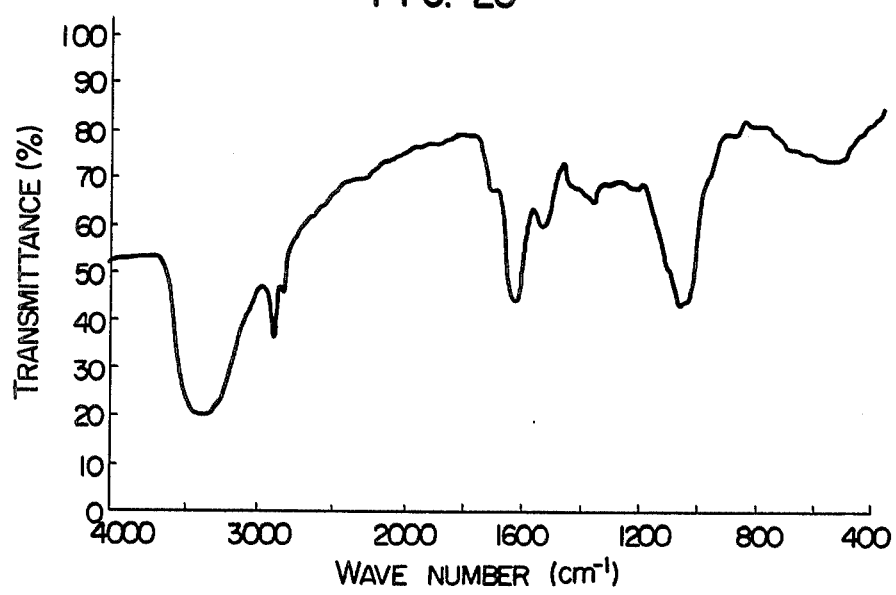
FIG. 23 shows an infrared absorption spectrum of the carcinostatic substance TF-310 (purified) obtained in Example 18, which appears hereinafter.
Figure 24:
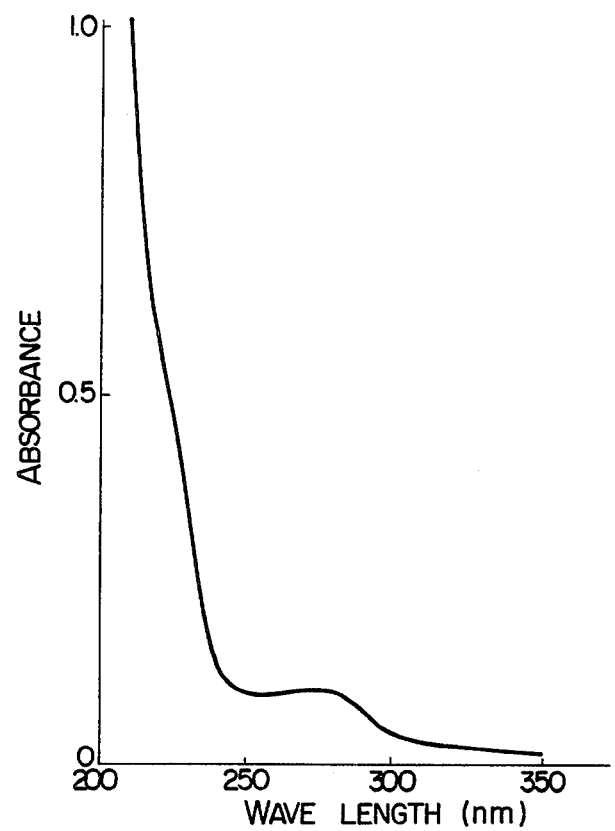
FIG. 24 shows an ultraviolet absorption spectrum of said substance.
Figure 25:
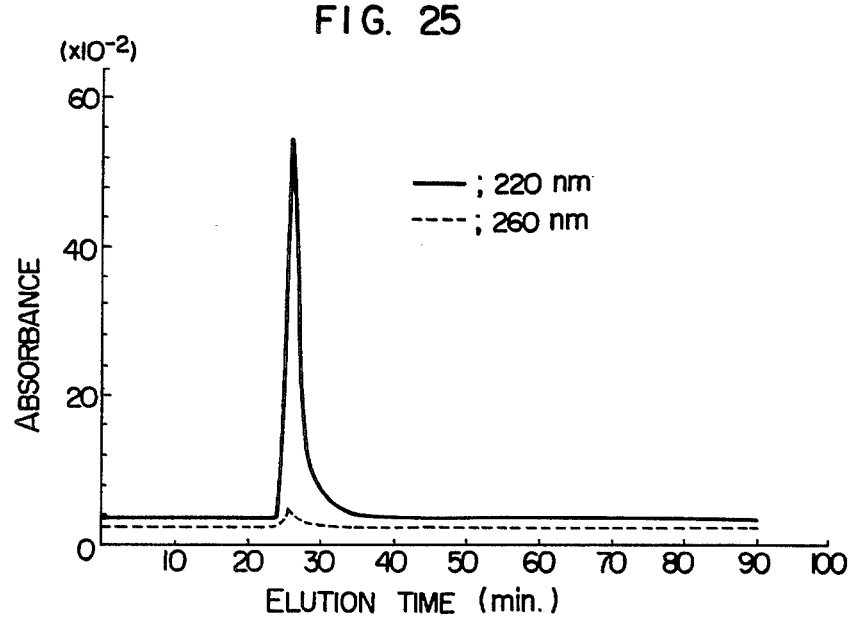
FIG. 25 shows a high performance liquid chromatogram of said substance.

The thus obtained carcinostatic substance TF-310 had the properties shown in Table 2 and the saccharide content thereof was generally about 16 to 30% in terms of glucose. The infrared absorption spectrum, ultraviolet absorption spectrum and high performance liquid chromatogram of a typical one are shown in FIGS. 23, 24 and 25, respectively.

EXAMPLE 19

In 10 ml of water was suspended 0.9 g of the carcinostatic substance TF-240 obtained in the same manner as in Example 7 (3), and 1N aqueous sodium hydroxide solution was added to the resulting suspension with stirring to adjust the pH to 7.8. After heating to 37° C., to the suspension were added 9 mg of Pronase E and several drops of toluene in this order. The resulting mixture was subjected, with shaking, to enzyme treatment at 37° to 40° C. at a pH of 7.8 to 8.0 for 24 hours. The treated mixture was subjected to centrifugation (4,000 r.p.m., 10 min) to separate the precipitate from the supernatant fluid. To the precipitate was added 3 ml of water having a pH of 8.0 and the resulting suspension was subjected to centrifugation (4,000 r.p.m., 10 min) to separate the precipitate from the washing. This washing and the above supernatant fluid were combined, and 1N hydrochloric acid was added to the combined solution to adjust the pH to 2.0, upon which a precipitate was formed. The resulting slurry was allowed to stand at 5° C. for 12 hours, and then subjected to centrifugation (1×10⁴ r.p.m., 10 min) to separate the precipitate from the supernatant fluid. To the precipitate was added 5 ml of water having a pH of 2.0 and the resulting suspension was subjected to centrifugation (1×10⁴ r.p.m., 10 min) to separate the precipitate from the washing. This washing and the above supernatant fluid were combined, and ethanol was added to the combined solution to form an 80% aqueous ethanol solution. The aqueous ethanol solution was stirred for 2 hours with ice-cooling and then subjected to centrifugation (1×10⁴ r.p.m., 10 min) to separate the precipitate from the supernatant fluid. This precipitate was washed with 5 ml of an 80% aqueous ethanol solution and 5 ml of ethanol in this order, and dried under reduced pressure to obtain 170 mg of the carcinostatic substance TF-340 fraction.

In 5 ml of water was dissolved 150 mg of this powder, and the pH of the resulting solution was adjusted to 7.0 by the addition of 1N aqueous sodium hydroxide solution. This solution was poured into a column packed with 25 ml of Amberlite IRA 400 preadjusted to the OH type by the use of 1N aqueous sodium hydroxide solution. Then, 100 ml of water was passed through the column and all the eluates were combined and adjusted to a pH of 7.0 by the addition of 1N hydrochloric acid. The solution obtained was concentrated under reduced pressure and filtered through a Millipore filter having a pore diameter of 0.3 μm and then freeze-dried to obtain 110 mg of the freeze-dried carcinostatic substance TF-340.

Figure 26:
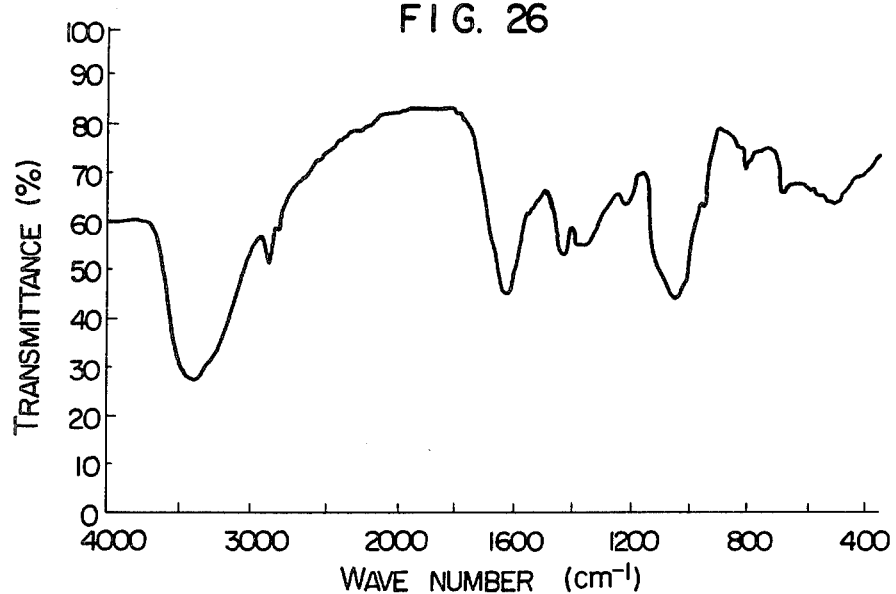
FIG. 26 shows an infrared absorption spectrum of the carcinostatic substance TF-340 obtained in Example 19, which appears hereinafter.
Figure 27:
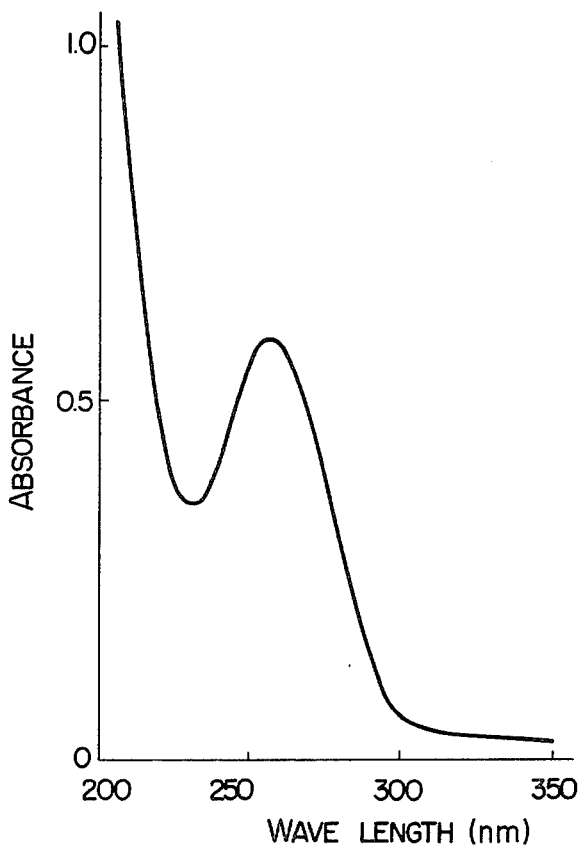
FIG. 27 shows an ultraviolet absorption spectrum of said substance.
Figure 28:
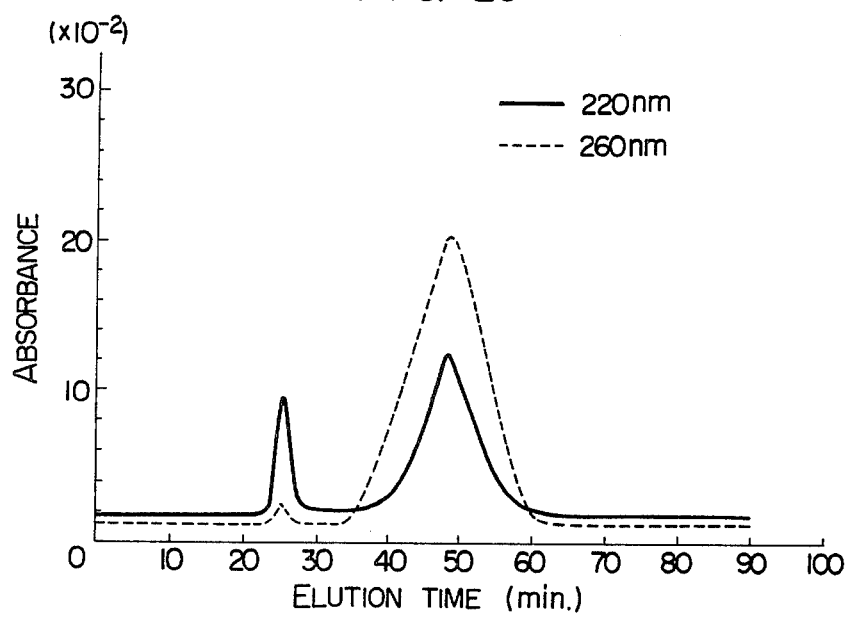
FIG. 28 shows a high performance liquid chromatogram of said substance.

The thus obtained carcinostatic substance TF-340 had the properties shown in Table 2, and the infrared absorption spectrum, ultraviolet absorption spectrum and high performance liquid chromatogram thereof are shown in FIGS. 26, 27 and 28, respectively.

EXAMPLE 20

In the same manner as in Example 19, 0.9 g of the carcinostatic substance TF-240 obtained in the same manner as in Example 8 was treated to obtain 115 mg of the freeze-dried carcinostatic substance TF-340.

The thus obtained carcinostatic substance TF-340 had the preperties shown in Table 2, and the infrared absorption spectrum, ultraviolet absorption spectrum and high performance liquid chromatogram thereof were substantially identical with those obtained in Example 19.

EXAMPLE 21

In the same manner as in Example 19, 0.9 g of the carcinostatic substance TF-240 obtained in Example 7 (3) was treated, except that (a) the enzyme treatment was carried out using 9 mg of trypsin (manufactured by Difco) in place of the Pronase E and (b), after the enzyme treatment, in collecting the precipitate from the water-soluble portion having a pH of 2.0, a 60% aqueous ethanol solution was formed in place of the 80% aqueous ethanol solution. Thus, 105 mg of the freeze-dried carcinostatic substance TF-340 was obtained.

The thus obtained carcinostatic substance TF-340 had the properties shown in Table 2, and the infrared absorption spectrum and ultraviolet absorption spectrum thereof were substantially identical with those obtained in Example 19.

EXAMPLE 22

The carcinostatic substance TF-240 obtained in Example 7 (3) was treated in the same manner as in Example 19, except that, after the enzyme treatment, in collecting the precipitate from the water-soluble portion having a pH of 2.0, a 60% aqueous ethanol solution was formed in place of the 80% aqueous ethanol solution. Thus, 101 mg of the freeze-dried carcinostatic substance TF-340 was obtained.

The thus obtained carcinostatic substance TF-340 had the properties shown in Table 2, and the infrared absorption spectrum, ultraviolet absorption spectrum and high performance liquid chromatogram thereof were substantially identical with those obtained in Example 19.

EXAMPLE 23

The carcinostatic substance TF-240 obtained in Example 7 (3) was subjected to the same enzyme treatment as in Example 19, after which in place of the collecting of the precipitate from the water-soluble portion having a pH of 2.0, the precipitate was collected by adding 40% trichloroacetic acid to a trichloroacetic acid concentration of 10% and forming the water-soluble portion thus obtained into an 80% aqueous ethanol solution, and subsequently the same treatments as in Example 19 were conducted to obtain 99 mg of the freeze-dried carcinostatic substance TF-340.

The thus obtained carcinostatic substance TF-340 had the properties shown in Table 2, and the infrared absorption spectrum, ultraviolet absorption spectrum and high performance liquid chromatogram thereof were substantially identical with those obtained in Example 19.

EXAMPLE 24

In 10 ml of water was suspended 0.82 g of the carcinostatic substance TF-250 obtained in the same manner as in Example 7 (4) and 1N aqueous sodium hydroxide solution was added thereto with stirring to adjust the pH to 7.8. After heating to 37° C., to the suspension were added 8 mg of Pronase E and several drops of toluene in this order. The resulting mixture was subjected, with shaking, to enzyme treatment at a pH of 7.8 to 8.0 at 37° to 40° C. for 24 hours. The treated mixture was subjected to centrifugation (4,000 r.p.m., 10 min) to separate the precipitate from the supernatant fluid. To the precipitate was added 3 ml of water having a pH of 8.0 and the resulting suspension was subjected to centrifugation (4,000 r.p.m., 10 min) to separate the precipitate from the washing. This washing and the above supernatant fluid were combined, 1N hydrochloric acid was added thereto to adjust the pH to 2.0, upon which a precipitate was formed. The resulting slurry was allowed to stand at 5° C. for 12 hours and then subjected to centrifugation ($1 \times 10^4$ r.p.m., 10 min) to separate the precipitate from the supernatant fluid. To the precipitate was added 5 ml of water having a pH of 2.0 and the resulting suspension was subjected to centrifugation ($1 \times 10^4$ r.p.m., 10 min) to separate the precipitate from the washing. This washing and the above supernatant fluid were combined, and ethanol was added to the combined solution to form an 80% aqueous ethanol solution. The aqueous ethanol solution was stirred for 2 hours with ice-cooling and then subjected to centrifugation ($1 \times 10^4$ r.p.m., 10 min) to separate the precipitate from the supernatant fluid. This precipitate was washed with 5 ml of an 80% aqueous ethanol solution and 5 ml of ethanol in this order, and dried under reduced pressure to obtain 430 mg of the carcinostatic substance TF-350 fraction.

In a 5 ml of water was dissolved 300 mg of this powder, and 1N aqueous sodium hydroxide solution was added to the resulting solution to adjust the pH to 7.0. This solution was poured into a column packed with 45 ml of Amberlite IRA 400 preadjusted to the OH type by the use of 1N aqueous sodium hydroxide solution. Then, 200 ml of water was passed through the column and all the eluates were combined and adjusted to a pH of 7.0 by the addition of 1N hydrochloric acid. The solution obtained was concentrated under reduced pressure and filtered through a Millipore filter having a pore diameter of 0.3 μm and then freeze-dried to obtain 260 mg of the freeze-dried carcinostatic substance TF-350.

Figure 29:
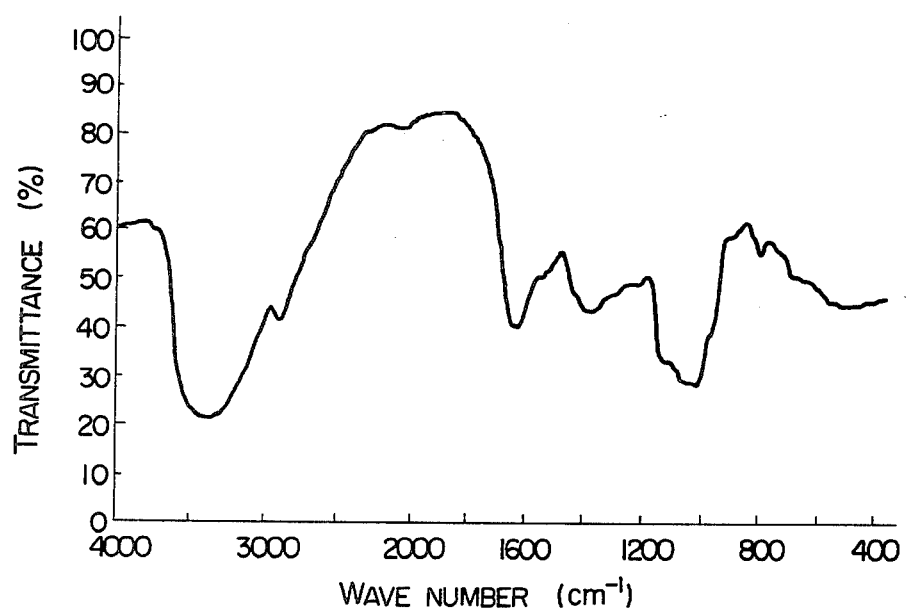
FIG. 29 shows an infrared absorption spectrum of the carcinostatic substance TF-350 obtained in Example 24, which appears hereinafter.
Figure 30:
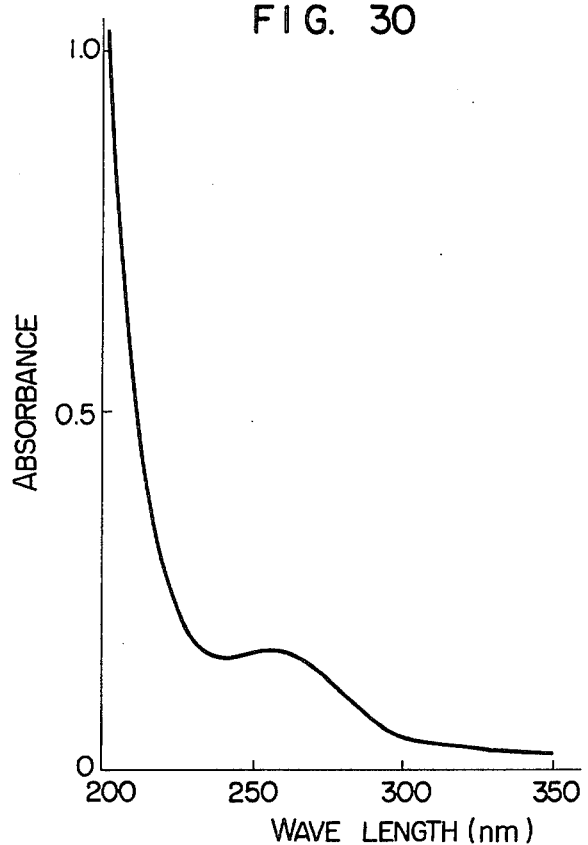
FIG. 30 shows an ultraviolet absorption spectrum of said substance.
Figure 31:
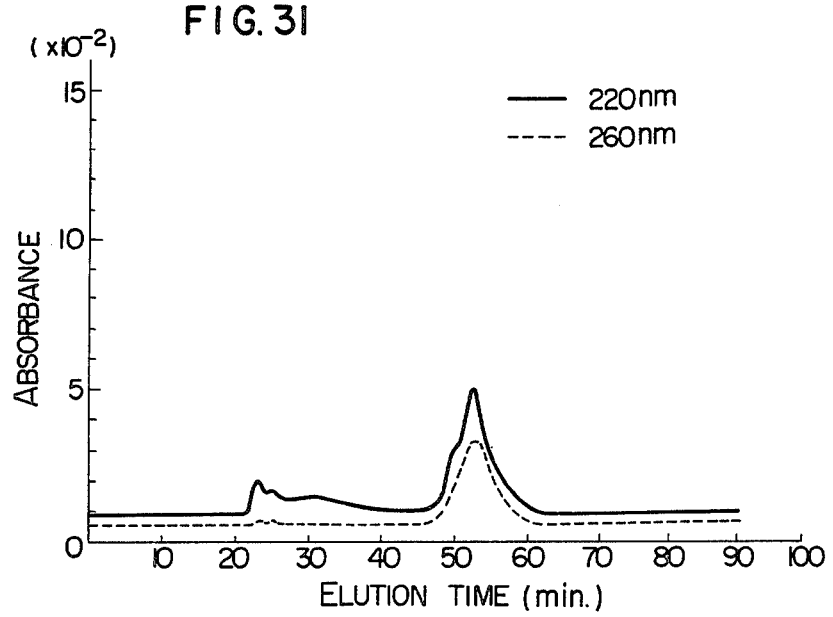
FIG. 31 shows a high performance liquid chromatogram of said substance.

The thus obtained carcinostatic substance TF-350 had the properties shown in Table 2, and the infrared absorption spectrum, ultraviolet absorption spectrum and high performance liquid chromatogram thereof are shown in FIGS. 29, 30 and 31, respectively.

EXAMPLE 25

In the same manner as in Example 24, 0.85 g of the carcinostatic substance TF-250 obtained in Example 9 was subjected to enzyme treatment by the use of 8 mg of Pronase E, to obtain 265 mg of the freeze-dried carcinostatic substance TF-350.

The thus obtained carcinostatic substance TF-350 had the properties shown in Table 2, and the infrared absorption spectrum, ultraviolet absorption spectrum and high performance liquid chromatogram thereof were substantially identical with those obtained in Example 24.

EXAMPLE 26

In the same manner as in Example 24, 0.80 g of the carcinostatic substance TF-250 obtained in Example 10 was subjected to enzyme treatment by the use of 8 mg of Pronase E, to obtain 253 mg of the freeze-dried carcinostatic substance TF-350.

The thus obtained carcinostatic substance TF-350 had the properties shown in Table 2, and the infrared absorption spectrum, ultraviolet absorption spectrum and high performance liquid chromatogram thereof were substantially identical with those obtained in Example 24.

EXAMPLE 27

In the same manner as in Example 24, 0.85 g of the carcinostatic substance TF-250 obtained in Example 7 (4) was treated, except that (a) the enzyme treatment was carried out using 8 mg of trypsin (product of Difco) in place of the Pronase E and (b), after the enzyme treatment, in collecting the precipitate from the water-soluble portion having a pH of 2.0, a 60% aqueous ethanol solution was prepared in place of the 80% aqueous ethanol solution, to obtain 247 mg of the freeze-dried carcinostatic substance TF-350.

The thus obtained carcinostatic substance TF-350 had the properties shown in Table 2, and the infrared absorption spectrum, ultraviolet absorption spectrum and high performance liquid chromatogram thereof were substantially identical with those obtained in Example 24.

EXAMPLE 28

0.85 g of the carcinostatic substance TF-250 obtained in the same manner as in Example 7 (4) was treated in the same manner as in Example 24, except that, after the enzyme treatment, in collecting the precipitate from the water-soluble portion having a pH of 2.0, a 60% aqueous ethanol solution was prepared in place of the 80% aqueous ethanol solution, to obtain 242 mg of the freeze-dried carcinostatic substance TF-350.

The thus obtained TF-350 had the properties shown in Table 2, and the infrared absorption spectrum, ultraviolet absorption spectrum and high performance liquid chromatogram thereof were substantially identical with those obtained in Example 24.

EXAMPLE 29

0.8 g of the carcinostatic substance TF-250 obtained in the same manner as in Example 7 (4) was subjected to the same enzyme treatment as in Example 24, after which in place of the collecting of the precipitate from the water-soluble portion having a pH of 2.0, the precipitate was collected by adding a 40% trichloroacetic acid to a trichloroacetic acid concentration of 10% and forming the water-soluble portion obtained into an 80% aqueous ethanol solution, and subsequently the same after-treatments as in Example 24 were conducted to obtain 238 mg of the freeze-dried carcinostatic substance TF-350.

The thus obtained carcinostatic substance TF-350 had the properties shown in Table 2, and the infrared absorption spectrum, ultraviolet absorption spectrum and high performance liquid chromatogram thereof were substantially identical with those obtained in Example 24.

PREPARATION EXAMPLE 1

A dilute aqueous sodium hydroxide solution was added to 3 to 4 mg of the carcinostatic substance TF-210 powder to form a solution having a pH of 7.0 to 7.5. The water-soluble portion of the resulting solution was charged into a vial and freeze-dried. This is dissolved, when used, in a sterilized physiological salt solution, a 0.5% lidocaine solution, a 5% aqueous glucose solution or the like, and the resulting solution is used as an injection.

PREPARATION EXAMPLE 2

A dilute aqueous sodium hydroxide solution was added to 2 to 3 mg of the carcinostatic substance TF-220 powder to form a solution having a pH of 7.0 to 7.5. The water-soluble portion of the resulting solution was charged into a vial and freeze-dried. This is dissolved, when used, in a sterilized physiological salt solution, a 0.5% lidocaine solution, a 5% aqueous glucose solution or the like, and the resulting solution is used as an injection.

PREPARATION EXAMPLE 3

A dilute aqueous sodium hydroxide solution was added to 1 mg of the carcinostatic substance TF-230 powder to form a solution having a pH of 7.0 to 7.5. This solution was charged into a vial and freeze-dried. This is dissolved, when used, in a sterilized physiological salt solution, a 0.5% lidocaine solution, a 5% aqueous glucose solution or the like, and the resulting solution is used as an injection.

PREPARATION EXAMPLE 4

A dilute aqueous sodium hydroxide solution was added to 1 mg of the carcinostatic substance TF-240 powder to form a solution having a pH of 7.0 to 7.5, and the solution was charged into a vial and freeze-dried. This is dissolved, when used, in a sterilized physiological salt solution, a 0.5% lidocaine solution, a 5% aqueous glucose solution or the like, and the resulting solution is used as an injection.

PREPARATION EXAMPLE 5

A dilute aqueous sodium hydroxide solution was added to 1 mg of the carcinostatic substance TF-250 powder to form a solution having a pH of 7.0 to 7.5, and the solution was charged into a vial and freeze-dried. This is dissolved, when used, in a sterilized physiological salt solution, a 0.5% lidocaine solution, a 5% aqueous glucose solution or the like, and the resulting solution is used as an injection.

PREPARATION EXAMPLE 6

An aqueous solution having a pH of 7.0 to 7.5 containing the carcinostatic substance TF-310-1 was charged into a vial, and freeze-dried to obtain a freeze-dried carcinostatic substance TF-310 preparation having a 0.5 or 1 mg unit. This is dissolved, when used, in a sterilized physiological salt solution, a 0.5% lidocaine solution, a 5% aqueous glucose solution, or the like, and the resulting solution is used as an injection.

PREPARATION EXAMPLE 7

An aqueous solution having a pH of 7.0 to 7.5 containing the carcinostatic substance TF-310-2 was charged into a vial, and freeze-dried to obtain a freeze-dried carcinostatic substance TF-310 preparation having a 0.5 or 1 mg unit. This is dissolved, when used, in a sterilized physiological salt solution, a 0.5% lidocaine solution, a 5% aqueous glucose solution or the like, and the resulting solution is used as an injection.

PREPARATION EXAMPLE 8

An aqueous solution having a pH of 7.0 to 7.5 containing the carcinostatic substance TF-320 was charged into a vial, and freeze-dried to a freeze-dried carcinostatic substance TF-320 preparation having 0.5 or 1 mg unit. This is dissolved, when used, in a sterilized physiological salt solution, a 0.5% lidocaine solution, a 5% aqueous glucose solution or the like, and the resulting solution is used as an injection.

PREPARATION EXAMPLE 9

An aqueous solution having a pH of 7.0 to 7.5 containing the carcinostatic substance TF-330 was charged into a vial, and freeze-dried to obtain a freeze-dried carcinostatic substance TF-330 preparation having 0.5 or 1 mg unit. This is dissolved, when used, in a sterilized physiological salt solution, a 0.5% lidocaine solution, a 5% aqueous glucose solution or the like, and the resulting solution is used as an injection.

PREPARATION EXAMPLE 10

An aqueous solution having a pH of 7.0 to 7.5 containing the carcinostatic substance TF-340 was charged into a vial, and freeze-dried to obtain a freeze-dried carcinostatic substance TF-340 preparation having 0.5 or 1 mg unit. This is dissolved, when used, in a sterilized physiological salt solution, a 0.5% lidocaine solution, a 5% aqueous glucose solution or the like, and the resulting solution is used as an injection.

PREPARATION EXAMPLE 11

An aqueous solution having a pH of 7.0 to 7.5 containing the carcinostatic substance TF-350 was charged into a vial, and freeze-dried to obtain a freeze-dried carcinostatic substance TF-350 preparation having 0.5 or 1 mg unit. This is dissolved, when used, in a sterilized physiological salt solution, a 0.5% lidocaine solution, a 5% aqueous glucose solution or the like, and the resulting solution is used as an injection.

What is claimed is:

1. A TF-210 product having the following properties, or an alkali metal or an alkaline earth metal salt thereof:
   (a) grayish white-light brown powder;
   (b) it prohibits the proliferation of Ehrlich ascites tumor, Ehrlich solid tumor, Sarcoma 180 and B-16 Melanoma of mouse, and has an immunostimulating activity;
   (c) it is insoluble in methanol, ethanol, acetone, benzene, chloroform, ethyl acetate and diethyl ether;
   (d) it has no clear melting point and decomposes at 160° to 235° C.;
   (e) its infrared absorption spectrum obtained by a KBr tablet method has absorption bands at approximately 3600–3200, 2950–2920, 1680–1620, 1550–1510, 1440, 1380, 1240–1220 and 1120–1020 $cm^{-1}$;
   (f) the ultraviolet absorption spectrum of an aqueous solution of its water-soluble fraction at a pH of 7.0 shows a strong absorption at the absorption edge, and shows an absorption peak at approximately 248–265 nm;
   (g) it is positive in Molisch reaction, phenolsulfuric acid reaction, anthrone-sulfuric acid reaction, indole-hydrochloric acid reaction and Lowry-Folin's reaction;
   (h) has elementary analysis values of C: 40–43% H: 5–7% N: 9–10%; and
   (i) the saccharide content of the water-soluble fraction at a pH of 7 as determined by a phenolsulfuric acid method is between about 5–25% by weight in terms of glucose, and the protein content determined by Lowry-Folin's method is between about 20–50% by weight in terms of bovine serum albumin.

2. A TF-220 product having the following properties, or an alkali metal or an alkaline earth metal salt thereof:
   (a) grayish white-light brown powder;
   (b) it prohibits the proliferation of Ehrlich ascites tumor, Ehrlich solid tumor, Sarcoma 180 and B-16 Melanoma of mouse, and has an immunostimulating activity;
   (c) it is insoluble in methanol, ethanol, acetone, benzene, chloroform, ethyl acetate and diethyl ether;
   (d) it has no clear melting point and decomposes at 160° to 240° C;
   (e) the infrared absorption spectrum obtained by a KBr tablet method has absorption bands at approximately 3600–3200, 2950–2920, 1680–1620, 1550–1510, 1440, 1380, 1240–1220 and 1120–1020 $cm^{-1}$;
   (f) the ultraviolet absorption spectrum of an aqueous solution of its water-soluble fraction at a pH of 7.0 shows a strong absorption at the absorption edge, and shows an absorption peak at approximately 248–266 nm;
   (g) it is positive in Molisch reaction, phenol-sulfuric acid reaction, anthrone-sulfuric acid reaction, indole-hydrochloric acid reaction and Lowry-Folin's reaction;
   (h) has elementary analysis values of C: 40–42% H: 5–7% N: 7–9%; and
   (i) the saccharide content of the water-soluble fraction at a pH of 7 as determined by a phenol-sulfuric acid method is between about 5–20% by weight in terms of glucose, and the protein content as determined by Lowry-Folin's method is about 10% by weight or less in terms of bovine serum albumin.

3. A TF-230 product having the following properties, or an alkali metal or an alkaline earth metal salt thereof:
   (a) grayish white-light brown powder;
   (b) it prohibits the proliferation of Ehrlich ascites tumor, Ehrlich solid tumor, Sarcoma 180 and B-16 Melanoma of mouse, and has an immunostimulating activity;
   (c) it is insoluble in methanol, ethanol, acetone, benzene, chloroform, ethyl acetate and diethyl ether;
   (d) it has no clear melting point and decomposes at 185° to 225° C;
   (e) the infrared absorption spectrum obtained by a KBr tablet method has absorption bands at approximately 3600–3200, 2950–2920, 1680–1620, 1550–1510, 1440, 1380, 1240–1220 and 1120–1020 $cm^{-1}$;
   (f) the ultraviolet absorption spectrum of its aqueous solution having a pH of 7.0 shows a strong absorption at the absorption edge, and shows an absorption peak at approximately 249–264 nm;
   (g) it is positive in Molisch reaction, phenol-sulfuric acid reaction, anthrone-sulfuric acid reaction, indole-hydrochloric acid reaction and Lowry-Folin's reaction;
   (h) has elementary analysis values of C: 42–45% H: 5–7% N: 10–11%; and
   (i) the saccharide content of the water-soluble fraction at a pH of 7 as determined by a phenol-sulfuric acid method is between about 5–25% by weight in terms of glucose, and the protein content as determined by Lowry-Folin's method is between about 30–60% by weight in terms of bovine serum albumin.

4. A TF-240 product having the following properties, or an alkali metal or an alkaline earth metal salt thereof:
   (a) grayish white-light brown powder;
   (b) it prohibits the proliferation of Ehrlich ascites tumor, Ehrlich solid tumor, Sarcoma 180 and B-16

Melanoma of mouse, and has an immunostimulating activity;
(c) it is insoluble in methanol, ethanol, acetone, benzene, chloroform, ethyl acetate and diethyl ether;
(d) it has no clear melting point and decomposes at 200° to 215° C.;
(e) the infrared absorption spectrum obtained by a KBr tablet method has absorption bands at approximately 3600–3200, 2950–2920, 1680–1620, 1550–1520, 1410–1360, 1280–1210, 1060, 960 and 820 cm$^{-1}$;
(f) the ultraviolet absorption spectrum of its aqueous solution having a pH of 7.0 shows a strong absorption at the absorption edge, and shows an absorption peak at approximately 250–265 nm;
(g) it is positive in Molisch reaction, phenol-sulfuric acid reaction, anthrone-sulfuric acid reaction, indole-hydrochloric acid reaction and Lowry-Folin's reaction;
(h) has elementary analysis values of C: 35–38% H: 4–5% N: 12–14%; and
(i) the saccharide content as determined by a phenol-sulfuric acid method is between about 15–35% by weight in terms of glucose; and the protein content as determined by Lowry-Folin's method is between about 20–30% by weight in terms of bovine serum albumin.

5. A TF-250 product having the following properties, or an alkali metal or an alkaline earth metal salt thereof:
(a) grayish white-light brown powder;
(b) it prohibits the proliferation of Ehrlich ascites tumor, Ehrlich solid tumor, Sarcoma 180 and B-16 Melanoma of mouse, and has an immunostimulating activity;
(c) it is soluble in water, but insoluble in methanol, ethanol, acetone, benzene, chloroform, ethyl acetate and diethyl ether;
(d) it has no clear melting point and decomposes at 165° to 210° C.;
(e) the infrared absorption spectrum obtained by a KBr tablet method has absorption bands at approximately 3600–3200, 2950–2920, 1680–1620, 1550–1510, 1410–1380, 1240–1210, 1150–1120, 1080–1020, 980 and 810 cm$^{-1}$;
(f) the ultraviolet absorption spectrum of its aqueous solution having a pH of 7.0 shows a strong absorption at the absorption edge, and shows an absorption peak at approximately 248–269 nm;
(g) it is positive in Molisch reaction, phenol-sulfuric acid reaction, anthrone-sulfuric acid reaction, indole-hydrochloric acid reaction and Lowry-Folin's reaction;
(h) has elementary analysis values of C: 30–33% H: 3–5% N: 3–5%; and
(i) the saccharide content as determined by a phenol-sulfuric acid method is between about 60–80% by weight in terms of glucose, and the protein content as determined by Lowry-Folin's method is between about 5–20% by weight in terms of bovine serum albumin.

6. A TF-300 (TF-310, TF-320 and TF-330) product having the following properties, or an alkali metal or an alkaline earth metal salt thereof:
(a) grayish white-light brown powder;
(b) it prohibits the proliferation of Ehrlich ascites tumor, Ehrlich solid tumor, Sarcoma 180 and B-16 Melanoma of mouse, and has an immunostimulating activity;
(c) it is soluble in water, but insoluble in methanol, ethanol, acetone, benzene, chloroform, ethyl acetate and diethyl ether;
(d) it has no clear melting point and begins to decompose at about 180° C. and remarkably decomposes at not less than 195° C.;
(e) the infrared absorption spectrum obtained by a KBr tablet method has absorption bands at approximately 3500–3300, 2920, 2850, 1660–1620, 1580–1540, 1460–1400, 1380–1360, 1120, 1080–1020, 970 and 820–800 cm$^{-1}$;
(f) the ultraviolet absorption spectrum of its aqueous solution having a pH of 7.0 shows a strong absorption at the absorption edge, and shows an absorption peak at approximately 246–280 nm;
(g) it is positive in Molisch reaction, phenol-sulfuric acid reaction, anthrone-sulfuric acid reaction, indole-hydrochloric acid reaction and Lowry-Folin's reaction, but negative in ninhydrin reaction;
(h) has elementary analysis values of C: 38–47% H: 5–7% N: 1–4%; and
(i) the saccharide content as determined by a phenol-sulfuric acid method is between about 16–60% by weight in terms of glucose, and the protein content as determined by Lowry-Folin's method is about 10% by weight or less in terms of bovine serum albumin.

7. A TF-300 (TF-310, TF-320, TF-330), product or an alkali metal or an alkaline earth metal salt thereof according to claim 6, wherein the saccharide content as determined by the phenol-sulfuric acid method is between about 16–30% by weight in terms of glucose.

8. A TF-300 (TF-310, TF-320, TF-330) product or an alkali metal or an alkaline earth metal salt thereof according to claim 6, wherein the saccharide content as determined by the phenol-sulfuric acid method is between about 20–60% by weight in terms of glucose.

9. A TF-340 product having the following properties, or an alkali metal or an alkali earth metal salt thereof;
(a) grayish white-light brown powder;
(b) it prohibits the proliferation of Ehrlich ascites tumor of mouse, and has an immunostimulating activity;
(c) it is soluble in water but insoluble in methanol, ethanol, acetone, benzene, chloroform, ethyl acetate and diethyl ether;
(d) it has no clear melting point and begins to decompose at about 140° C. and decomposes remarkably at 200° C. or more;
(e) the infrared absorption spectrum obtained by a KBr tablet method has absorption bands at approximately 3500–3300, 2920, 2850, 1660–1640, 1580–1520, 1460–1440, 1410–1340, 1250–1220, 1120–1030, 970 and 835 cm$^{-1}$;
(f) the ultraviolet absorption spectrum of its aqueous solution having a pH of 7.0 shows a strong absorption at the absorption edge, and shows an absorption peak at approximately 250–265 nm;
(g) it is positive in Molisch reaction, phenol-sulfuric acid reaction, anthrone-sulfuric acid reaction, indole-hydrochloric acid reaction and Lowry-Folin's reaction, but negative in ninhydrin reaction;
(h) has elementary analysis values of C: 32–34% H: 4–6% N: 3–5%; and
(i) the saccharide content as determined by a phenol-sulfuric acid method is between about 20–50% by weight in terms of glucose, and the protein content as determined by Lowry-Folin's method is about 10% by weight or less in terms of bovine serum albumin.

10. A TF-350 product having the following properties, or an alkali metal or an alkaline earth metal salt thereof;

(a) grayish white-light brown powder;

(b) it prohibits the proliferation of Ehrlich ascites tumor of mouse, and has an immunostimulating activity;

(c) it is soluble in water, but insoluble in methanol, ethanol, acetone, benzene, chloroform, ethyl acetate and diethyl ether;

(d) it has no clear melting point, and begins to decompose at about 110° C. and decomposes remarkably at 180° C. or more;

(e) the infrared absorption spectrum obtained by a KBr tablet method has absorption bands at approximately 3500–3300, 2920–2900, 1660–1630, 1580–1520, 1460–1340, 1140–1100, 1080–1020, 970 and 820–800 cm$^{-1}$;

(f) the ultraviolet absorption spectrum of its aqueous solution having a pH of 7.0 shows a strong absorption at the absorption edge, and shows an absorption peak at approximately 245–264 nm;

(g) it is positive in Molisch reaction, phenol-sulfuric acid reaction, anthrone-sulfuric acid reaction, indole-hydrochloric acid reaction and Lowry-Folin's reaction but negative in ninhydrin reaction;

(h) has elementary analysis values of C: 34–37% H: 5–6% N: 1–2%; and (i) the saccharide content as determined by a phenol-sulfuric acid method is between about 80–95% by weight in terms of glucose, and the protein content as determined by Lowry-Folin's method is about 10% by weight or less in terms of bovine serum albumin.

11. A composition comprising a product selected from the group consisting of TF-2 (TF-210, TF-220, TF-230, TF-240, TF-250, TF-300 (TF-310, TF-320, TF-330), TF-340, or TF-350) and an alkali metal or an alkaline earth metal salt thereof according to any one of claims 1 to 10.

12. The composition according to claim 11 comprising a product selected from the group consisting of TF-300 (TF-310, TF-320, or TF-330) and an alkali metal or an alkaline earth metal salt thereof.

* * * * *